US011610347B2

(12) United States Patent
Lee et al.

(10) Patent No.: US 11,610,347 B2
(45) Date of Patent: Mar. 21, 2023

(54) TOMOGRAPHIC IMAGE PROCESSING APPARATUS AND METHOD

(71) Applicant: Samsung Electronics Co., Ltd., Suwon-si (KR)

(72) Inventors: Chang-lae Lee, Seoul (KR); Duhgoon Lee, Yongin-si (KR); Seung-wan Lee, Daejeon (KR); Woo-young Jang, Seongnam-si (KR); Jin-wook Jung, Seoul (KR); Kyoung-yong Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 55 days.

(21) Appl. No.: 16/636,130

(22) PCT Filed: Aug. 2, 2018

(86) PCT No.: PCT/KR2018/008785
§ 371 (c)(1),
(2) Date: Feb. 3, 2020

(87) PCT Pub. No.: WO2019/027270
PCT Pub. Date: Feb. 7, 2019

(65) Prior Publication Data
US 2021/0110583 A1 Apr. 15, 2021

(30) Foreign Application Priority Data

Aug. 3, 2017 (KR) .................. 10-2017-0098624
May 17, 2018 (KR) .................. 10-2018-0056771

(51) Int. Cl.
G06T 11/00 (2006.01)
A61B 6/03 (2006.01)
(Continued)

(52) U.S. Cl.
CPC ............ *G06T 11/008* (2013.01); *A61B 6/032* (2013.01); *A61B 6/4241* (2013.01); *A61B 6/461* (2013.01);
(Continued)

(58) Field of Classification Search
CPC ..................... G06T 11/008; G06T 7/62; G06T 2207/10081; G06T 2207/20104;
(Continued)

(56) References Cited

U.S. PATENT DOCUMENTS 7,724,865 B2    5/2010   Wu et al.
8,055,039 B2   11/2011   Wu et al.
(Continued)

FOREIGN PATENT DOCUMENTS

KR    10-2013-0111629    10/2013
KR    10-2014-0048671    4/2014
(Continued)

OTHER PUBLICATIONS

International Search Report dated Nov. 15, 2018 in corresponding International Patent Application No. PCT/KR2018/008785.
(Continued)

*Primary Examiner* — Courtney D Thomas
(74) *Attorney, Agent, or Firm* — Staas & Halsey LLP

(57) ABSTRACT

A computed tomography (CT) image processing apparatus and a CT image processing method are provided. The CT image processing apparatus may generate a virtual monochromatic image (VMI) by applying a weight to each of first, second, and third images corresponding to three different energy ranges. The CT image processing apparatus may set a region of interest (ROI) on a CT image, determine a VMI at an energy level at which a CNR of the ROI is at a maximum among a plurality of VMIs, and display the determined VMI.

15 Claims, 16 Drawing Sheets

(51) Int. Cl.
*A61B 6/00* (2006.01)
*G06T 7/62* (2017.01)

(52) U.S. Cl.
CPC ............ *A61B 6/469* (2013.01); *A61B 6/5294* (2013.01); *A61B 6/583* (2013.01); *G06T 7/62* (2017.01); *A61B 6/481* (2013.01); *G06T 2207/10081* (2013.01); *G06T 2207/20104* (2013.01); *G06T 2207/20216* (2013.01); *G06T 2207/30056* (2013.01); *G06T 2207/30096* (2013.01); *G06T 2211/408* (2013.01)

(58) Field of Classification Search
CPC . G06T 2207/20216; G06T 2207/30056; G06T 2207/30096; G06T 2211/408; G06T 5/50; G06T 11/003; A61B 6/032; A61B 6/4241; A61B 6/461; A61B 6/469; A61B 6/5294; A61B 6/583; A61B 6/481; A61B 6/482; A61B 5/03; A61B 5/055; A61B 8/00; A61B 5/032

See application file for complete search history.

(56) References Cited

U.S. PATENT DOCUMENTS

| | | | |
|---|---|---|---|
| 9,448,310 | B2 | 9/2016 | Han et al. |
| 9,492,133 | B2 | 11/2016 | Kang et al. |
| 9,693,742 | B2 | 7/2017 | Grasruck et al. |
| 2009/0052612 | A1* | 2/2009 | Wu ............... A61B 6/4241 378/5 |
| 2014/0005533 | A1 | 1/2014 | Grasruck et al. |
| 2014/0185758 | A1 | 7/2014 | Kang et al. |
| 2017/0023498 | A1 | 1/2017 | Worstell et al. |
| 2017/0172528 | A1 | 6/2017 | Wiedmann et al. |

FOREIGN PATENT DOCUMENTS

| | | |
|---|---|---|
| KR | 10-2014-0052563 | 5/2014 |
| KR | 10-2014-0084659 | 7/2014 |
| KR | 10-1485902 | 1/2015 |
| KR | 10-2016-0056979 | 5/2016 |
| KR | 10-2017-0078180 | 7/2017 |

OTHER PUBLICATIONS

Written Opinion of the International Searching Authority dated Nov. 15, 2018 in corresponding International Patent Application No. PCT/KR2018/008785.

Extended European Search Report dated Jun. 19, 2020 in European Patent Application No. 18841343.9.

Lifeng Yu et al., "Virtual monochromatic imaging in dual-source dual-energy CT: Radiation dose and image quality", Med. Phys. vol. 38, No. 12, Dec. 2011, 9 pages.

European Office Action dated Apr. 25, 2022 from European Application No. 18841343.9.

Korean Office Action dated Oct. 13, 2022 in Korean Patent Application No. 10-2018-0056771 (7 pages; 6 pages English translation).

* cited by examiner

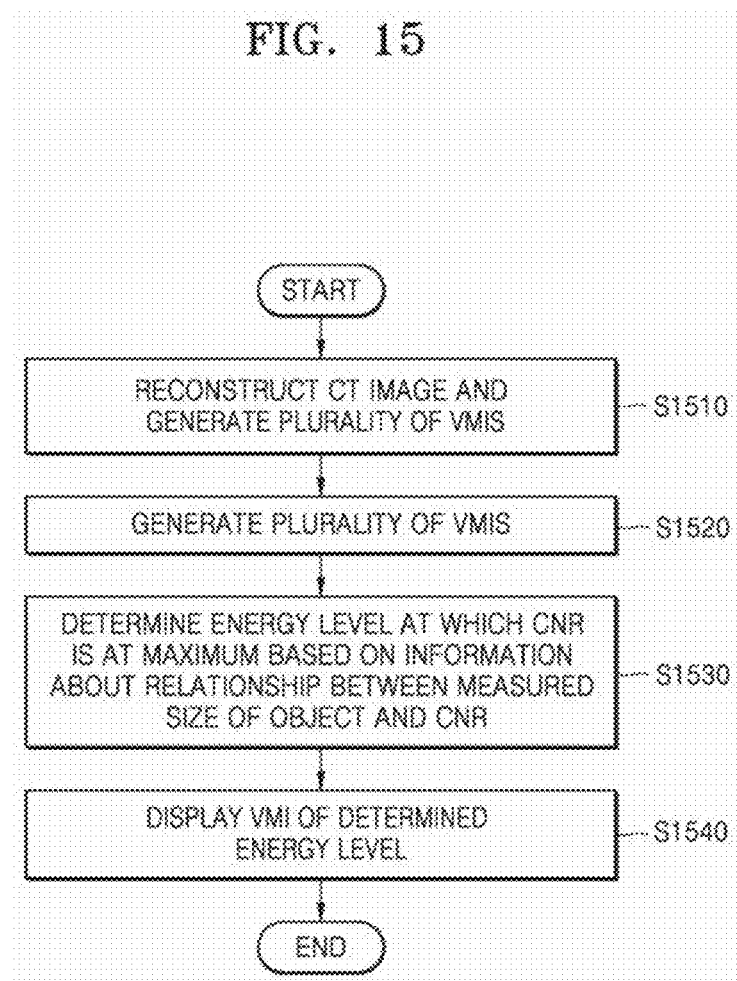

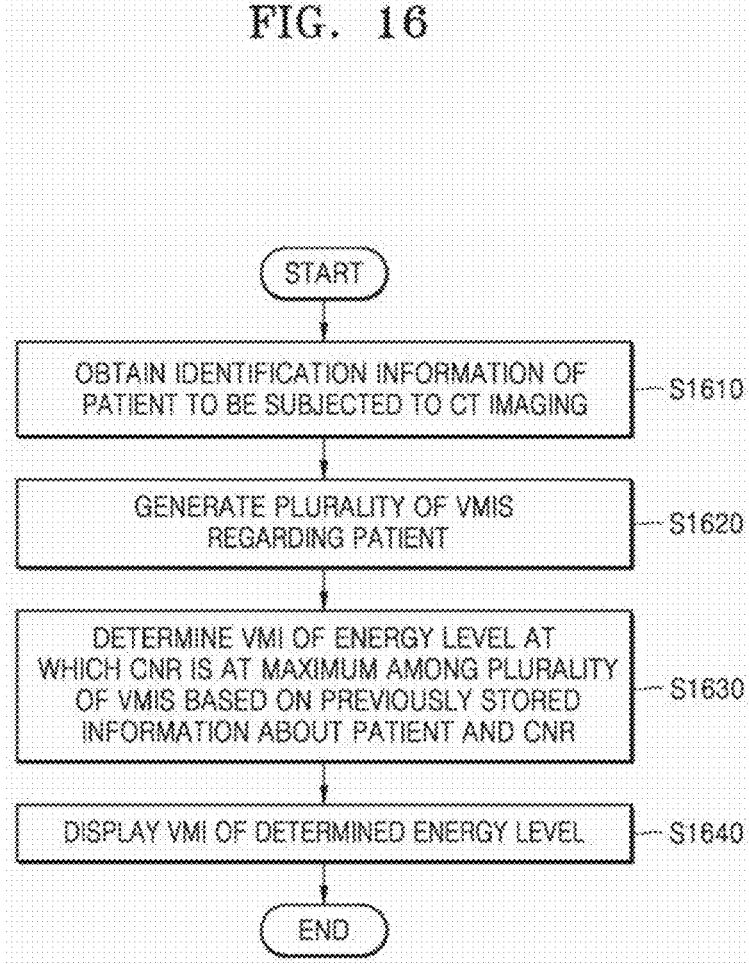

_US 11,610,347 B2_

TOMOGRAPHIC IMAGE PROCESSING APPARATUS AND METHOD

CROSS-REFERENCE TO RELATED APPLICATIONS

This application is a U.S. National Stage Application which claims the benefit under 35 U.S.C. § 371 of International Patent Application No. PCT/KR2018/008785 filed on Aug. 2, 2018, which claims foreign priority benefit under 35 U.S.C. § 119 of Korean Patent Application Nos. 10-2017-0098624 and 10-2018-0056771 filed on Aug. 3, 2017, and May 17, 2018, in the Korean Intellectual Property Office, the contents of all of which are incorporated herein by reference.

TECHNICAL FIELD

The disclosure relates to apparatuses and methods for processing computed tomography (CT) images.

BACKGROUND ART

A computed tomography (CT) image processing apparatus is an apparatus for obtaining images of an internal structure of an object. The CT image processing apparatus is a non-invasive test apparatus which captures and processes images of structural details, internal tissues and fluid flow in an object and displays the same to a user. The user, such as a doctor, may diagnose a health condition and disease of a patient by using a CT image output from the CT image processing apparatus. Therefore, to diagnose a disease precisely, a method of obtaining a tomography image capable of more clearly distinguishing different substances present inside the object is needed.

In CT using dual-energy X-rays, a virtual monochromatic imaging method of generating a diagnostic image by using a method of calculating a weight average of tomography images obtained using low energy and high energy is known. The virtual monochromatic imaging method may reduce an amount of radiation that the object is exposed to.

DESCRIPTION OF EMBODIMENTS

Technical Problem

Provided are computed tomography (CT) image processing apparatuses configured to generate a plurality of virtual monochromatic images (VMIs) respectively corresponding to a plurality of energy levels and display virtual monochromatic energy at an energy level having an optimal noise level for the clearest possible observation of a lesion of an object among the plurality of generated VMIs, and methods of operating the same.

Solution to Problem

The CT image processing apparatus according to an embodiment may generate a VMI by applying a weight to each of first, second, and third images corresponding to three different energy periods.

According to an embodiment of the disclosure, provided is a computed tomography (CT) image processing apparatus including a data obtainer configured to detect X-rays having different energy spectra transmitted through an object and obtain raw data in each of energy ranges of the X-rays, through the detected X-rays; a processor configured to generate a CT image by using the raw data, set a region of interest (ROI) on the CT image based on a user input, generate a plurality of virtual monochromatic images (VMIs) respectively corresponding to a plurality of energy levels by reconstructing the CT image, measure a contrast-to-noise ratio (CNR) of the ROI, and determine a VMI at an energy level at which the measured CNR is at a maximum among the plurality of VMIs; and a display configured to display the determined VMI.

Advantageous Effects of Disclosure

A CT image processing apparatus according to an embodiment of the disclosure may automatically determine the energy level at which a contrast-to-noise ratio (CNR) is the maximum among a plurality of virtual monochromatic images (VMIs) 800 respectively corresponding to a plurality of energy levels, and display the VMI of the determined energy level, thereby improving the user convenience and increasing the accuracy of diagnosis.

BRIEF DESCRIPTION OF DRAWINGS

FIG. 15 is a flowchart showing a method of determining a VMI of an energy level at which a CNR is the maximum based on a size of an object, the method being performed by a CT image processing apparatus, according to an embodiment.

FIG. 16 is a flowchart showing a method of determining a VMI of an energy level at which a CNR is the maximum based on identification information of a patient, the method being performed by a CT image processing apparatus, according to an embodiment.

BEST MODE

Figure 1:
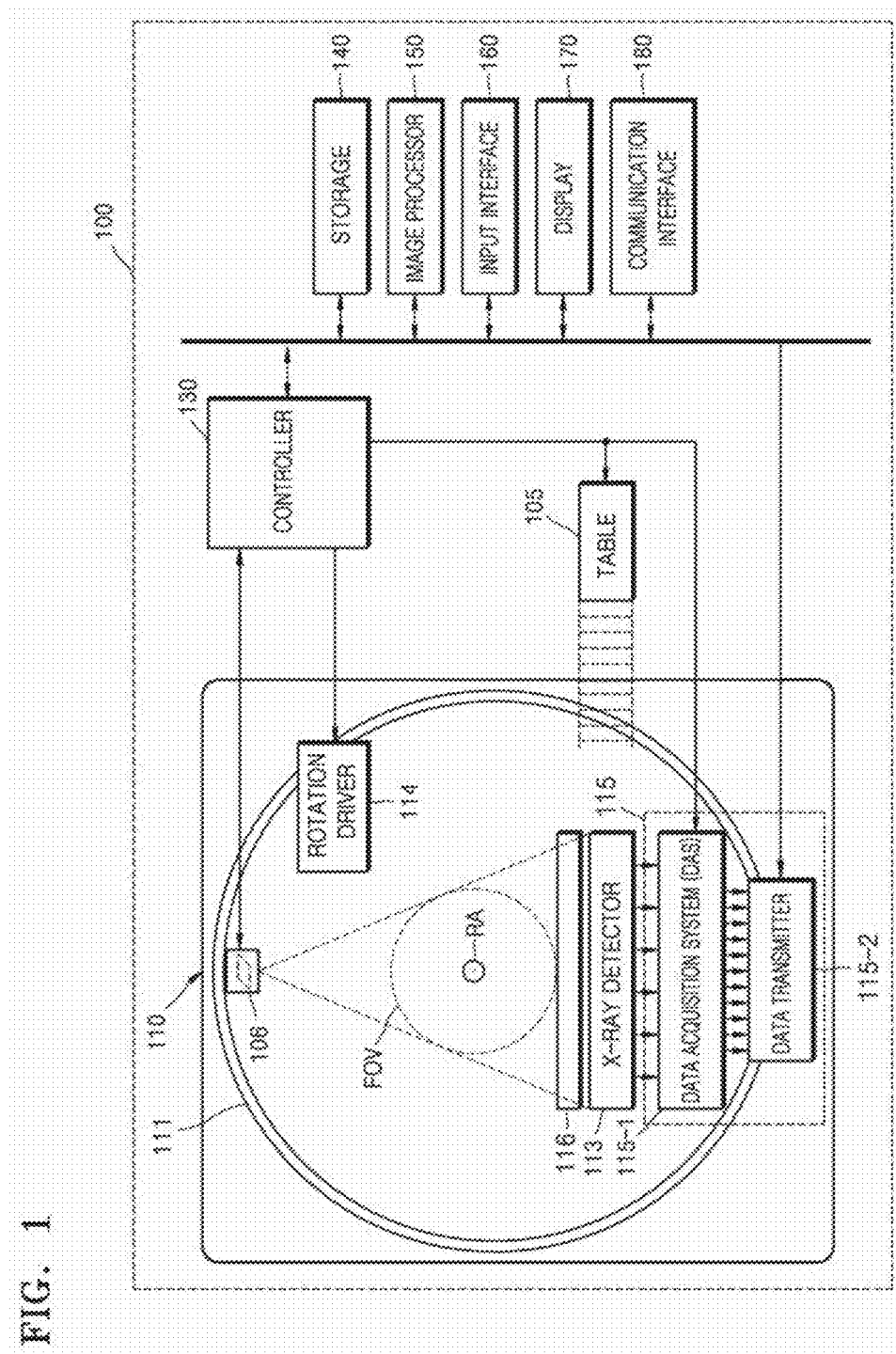
FIG. 1 illustrates a structure of a computed tomography (CT) system according to an embodiment.

According to an embodiment of the disclosure, provided is a computed tomography (CT) image processing apparatus including a data obtainer configured to detect X-rays having different energy spectra transmitted through an object and obtain raw data in each of energy ranges of the X-rays, through the detected X-rays; a processor configured to generate a CT image by using the raw data, set a region of interest (ROI) on the CT image based on a user input, generate a plurality of virtual monochromatic images (VMIs) respectively corresponding to a plurality of energy levels by reconstructing the CT image, measure a contrast-to-noise ratio (CNR) of the ROI, and determine a VMI at an energy level at which the measured CNR is at a maximum among the plurality of VMIs; and a display configured to display the determined VMI.

For example, the data obtainer may be further configured to detect X-rays having different energy spectra transmitted through the object by dividing the X rays into three energy ranges and obtain first raw data to third raw data respectively corresponding to the three energy ranges by amplifying the detected X rays, and the processor is further configured to reconstruct the first raw data to third raw data to generate first to third CT images, calculate a weighted function applied to each of the first to third CT images, and calculate a weighted average of the first to third CT images to generate the plurality of VMIs respectively corresponding to the plurality of energy levels.

For example, the data obtainer may include a photon counting detector (PCD) configured to divide the X-rays having different energy spectrums into the three energy ranges and detect photons having energy levels respectively corresponding to the three energy ranges.

For example, the CT image processing apparatus may further include a user input unit configured to receive a user input designating at least one of a blood vessel, tissue, and a background region on the CT image, wherein the processor is configured to set the at least one of the blood vessel, the tissue, and the background region on the CT image as the ROI, based on the received user input.

For example, the CT image processing apparatus may further include a user input unit configured to receive information about a type of a contrast agent from a user, wherein the processor is configured to measure a concentration of the contrast agent injected into the object in the ROI and determine the energy level at which the CNR is maximum based on the type of the contrast agent input through the user input unit and a relationship between the concentration of the contrast agent and the CNR.

For example, the CT image processing apparatus may further include a memory storing, in a look-up table (LUT), information about the relationship between the energy level and the CNR according to the type and the concentration of the contrast agent, wherein the processor is further configured to determine the VMI of the energy level at which the CNR is at a maximum according to the concentration of the contrast agent determined in the ROI and the type of the contrast agent, with reference to the LUT stored in the memory.

For example, the processor may be further configured to measure a size of the object in the CT image and, based on the measured size of the object, determine the VMI of the energy level at which the CNR is at a maximum.

For example. the CT image processing apparatus may further include a memory storing, in a look-up table (LUT), information about a relationship between the energy level and the CNR, according to the size of the object, wherein the processor is further configured to determine a VMI of the energy level at which the CNR is at a maximum according to the measured size of the object, with reference to the LUT stored in the memory.

For example, the processor may be further configured to measure the size of the object through sizes of various phantoms having diameters of different sizes.

For example, the CT image processing apparatus further includes a memory storing information about the energy level at which the CNR is at a maximum, according to information of a patient, wherein the processor is further configured to obtain identification information of the patient who is a target of CT photographing and, based on the information about the energy level stored in the memory, determine the VMI of the energy level at which the CNR is at a maximum according to the identification information of the patient.

According to another embodiment of the disclosure, provided is a method of operating a computed tomography (CT) image processing apparatus, the method including: detecting X-rays having different energy spectra transmitted through the object and obtaining raw data in each of energy ranges through the detected X-rays; setting a region of interest (ROI) on the CT image based on a user input; generating a plurality of virtual monochromatic images (VMIs) respectively corresponding to a plurality of energy levels by reconstructing the CT image; determining a contrast-to-noise ratio (CNR) of the ROI on the plurality of VMIs and determining a VMI at an energy level at which the determined CNR is at a maximum among the plurality of VMIs; and displaying the determined VMI.

For example, the generating of the plurality of VMIs may include detecting X-rays having different energy spectra transmitted through the object by dividing the X rays into three energy ranges and obtaining first raw data to third raw data corresponding to respectively the three energy ranges by amplifying the detected X rays; reconstructing the first raw data to third raw data and generating first to third CT images; calculating a weighted function applied to each of the first to third CT images; and calculating a weighted average of the first to third CT images and generating the plurality of VMIs respectively corresponding to the plurality of energy levels.

For example, the setting of the ROI may include: receiving a user input designating at least one of a blood vessel, tissue, and a background region on the CT image; and setting the at least one of the blood vessel, the tissue, and the background region on the CT image as the ROI, based on the received user input.

For example, the determining of the VMI may include: measuring a concentration of a contrast agent injected into the object in the ROI; receiving information about a type of the contrast agent from a user; and determining the energy level at which the CNR is at a maximum based on the type of the contrast agent and a relationship between the concentration of the contrast agent and the CNR.

For example, the CT image processing apparatus stores, in a look-up table (LUT), information about the relationship between the energy level and the CNR according to the type and the concentration of the contrast agent, wherein the determining of the VMI includes determining a VMI at the energy level at which the CNR is at a maximum according to the concentration of the contrast agent determined in the ROI and the type of the contrast agent, with reference to the LUT stored in the CT image processing apparatus.

For example, the method may further include measuring a size of the object in the CT image, wherein the determining of the VMI includes determining the VMI at the energy level at which the CNR is at a maximum based on the measured size of the object.

For example, the CT image processing apparatus may store, in a look-up table (LUT), information about a relationship between the energy level and the CNR according to the size of the object, wherein the determining of the VMI includes determining the VMI of the energy level at which the CNR is at a maximum according to the measured size of the object, with reference to the previously stored LUT.

For example, the measuring of the size of the object may include measuring the size of the object through sizes of various phantoms having diameters of different sizes.

For example, the CT image processing apparatus may store information about the energy level at which the CNR is at a maximum according to information of a patient, wherein the determining of the VMI includes: obtaining identification information of the patient who is a target of CT photographing; and based on the information about the energy level stored in the memory, determining the VMI at the energy level at which the CNR is at a maximum according to the identification information of the patient.

According to another embodiment of the disclosure provided is a computer program product including a non-transitory computer readable storage medium, wherein the non-transitory computer readable storage medium includes instructions to perform: detecting X-rays having different energy spectra transmitted through the object and obtaining raw data in each of energy ranges through the detected X-rays; setting a region of interest (ROI) on the CT image based on a user input; generating a plurality of virtual monochromatic images (VMIs) respectively corresponding to a plurality of energy levels by reconstructing the CT image; determining a contrast-to-noise ratio (CNR) of the ROI on the plurality of VMIs and determining a VMI at an energy level at which the determined CNR is at a maximum among the plurality of VMIs; and displaying the determined VMI.

MODE OF DISCLOSURE

The principle of the present disclosure is explained and embodiments are disclosed so that the scope of the present disclosure is clarified and one of ordinary skill in the art to which the present disclosure pertains implements the present disclosure. The disclosed embodiments may have various forms.

Throughout the specification, like reference numerals or characters refer to like elements. In the present specification, all elements of embodiments are not explained, but general matters in the technical field of the present disclosure or redundant matters between embodiments will not be described. Terms 'module' or 'unit' used herein may be implemented using at least one or a combination from among software, hardware, or firmware, and, according to embodiments, a plurality of 'module' or 'unit' may be implemented using a monochromatic element, or a monochromatic 'module' or 'unit' may be implemented using a plurality of units or elements. The operational principle of the present disclosure and embodiments thereof will now be described more fully with reference to the accompanying drawings.

In the present specification, an image may include a medical image obtained by a medical imaging apparatus, such as a computed tomography (CT) apparatus, a magnetic resonance imaging (MRI) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

In the present specification, a 'CT system' or 'CT apparatus' refers to a system or apparatus configured to emit X-rays while rotating around at least one axis relative to an object and photograph the object by detecting the X-rays.

In the specification, a 'CT image' refers to an image constructed from raw data obtained by photographing an object by detecting X-rays that are emitted as the CT system or apparatus rotates about at least one axis with respect to the object.

FIG. 1 illustrates a structure of a CT system 100 according to an embodiment.

The CT system 100 may include a gantry 110, a table 105, a controller 130, a storage 140, an image processor 150, an input interface 160, a display 170, and a communication interface 180.

The gantry 110 may include a rotating frame 111, an X-ray generator 112, an X-ray detector 113, a rotation driver 114, and a readout device 115.

The rotating frame 111 may receive a driving signal from the rotation driver 114 and rotate around a rotation axis (RA).

An anti-scatter grid 116 may be disposed between an object and the X-ray detector 113 and may transmit most of primary radiation and attenuate scattered radiation. The object may be positioned on the table 105 which may move, tilt, or rotate during a CT scan.

The X-ray generator 112 receives a voltage and a current from a high voltage generator (HVG) to generate and emit X-rays.

The CT system 100 may be implemented as a monochromatic-source CT system including one X-ray generator 112 and one X-ray detector 113, or as a dual-source CT system including two X-ray generators 112 and two X-ray detectors 113.

The X-ray detector 113 detects radiation that has passed through the object. For example, the X-ray detector 113 may detect radiation by using a scintillator, a photon counting detector, etc.

Methods of driving the X-ray generator 112 and the X-ray detector 113 may vary depending on scan modes used for scanning of the object. The scan modes are classified into an axial scan mode and a helical scan mode, according to a path along which the X-ray detector 113 moves. Furthermore, the scan modes are classified into a prospective mode and a retrospective mode, according to a time interval during which X-rays are emitted.

The controller 130 may control an operation of each of the components of the CT system 100. The controller 130 may include a memory configured to store program for performing a function or data and a processor configured to process the program codes or the data. The controller 130 may be implemented in various combinations of at least one memory and at least one processor. The processor may generate or delete a program module according to an operating status of the CT system 100 and process operations of the program module.

The readout device 115 receives a detection signal generated by the X-ray detector 113 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 113, and outputs the amplified signal. The data transmitter 115-2 uses a circuit such as a multiplexer (MUX) to output the signal amplified in the DAS 115-1 to the image processor 150. According to a slice thickness or a number of slices, only some of a plurality of pieces of data collected by the X-ray detector 113 may be provided to the image processor 150, or the image processor 150 may select only some of the plurality of pieces of data.

The image processor 150 obtains tomography data from a signal obtained by the readout device 115 (e.g., pure data that is data before being processed). The image processor 150 may pre-process the obtained signal, convert the obtained signal into tomography data, and post-process the tomography data. The image processor 150 may perform some or all of the processes described herein, and the type or order of processes performed by the image processor 150 may vary according to embodiments.

The image processor 150 may perform pre-processing, such as a process of correcting sensitivity irregularity between channels, a process of correcting a rapid decrease of signal strength, or a process of correcting signal loss due to an X-ray absorbing material, on the signal obtained by the readout device 115.

According to embodiments, the image processor 150 may perform some or all of the processes for reconstructing a tomography image, to thereby generate the tomography data. According to an embodiment, the tomography data may be in the form of data that has undergone back-projection, or in the form of a tomography image. According to embodiments, additional processing may be performed on the tomography data by an external device such as a server, a medical apparatus, or a portable device.

The CT system 100 performs CT on the object to obtain raw data to obtain the CT image. The CT system 100 generates X-rays, irradiates the X-rays to the object, and detects the X-rays passing through the object by using the X-ray detector 113. The X-ray detector 113 generates the raw data corresponding to the detected X-ray. The raw data may refer to data before being reconstructed as the CT image by the image processor 150. The raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomography image is obtained by using image reconstruction techniques including back-projection of the raw data.

The storage 140 is a storage medium for storing control-related data, image data, etc., and may include a volatile or non-volatile storage medium.

The input interface 160 receives control signals, data, etc., from a user. The display 170 may display information indicating an operational status of the CT system 100, medical information, medical image data, etc.

The CT system 100 includes the communication interface 180 and may be connected to external devices, such as a server, a medical apparatus, and a portable device (smartphone, tablet personal computer (PC), wearable device, etc.), via the communication interface 180.

The communication interface 180 may include one or more components that enable communication with an external device. For example, the communication interface 180 may include a short distance communication module, a wired communication module, and a wireless communication module.

The communication interface 180 may receive control signals and data from an external device and transmit the received control signals to the controller 130 so that the controller 130 may control the CT system 100 according to the received control signals.

Alternatively, by transmitting a control signal to an external device via the communication interface 180, the controller 130 may control the external device according to the control signal.

For example, the external device may process data according to a control signal received from the controller 130 via the communication interface 180.

A program for controlling the CT system 100 may be installed on the external device and may include instructions for performing some or all of the operations of the controller 130.

The program may be preinstalled on the external device, or a user of the external device may download the program from a server that provides an application for installation. The server that provides an application may include a recording medium having the program recorded thereon.

According to embodiments, the CT system 100 may or may not use contrast media during a CT scan, and may be implemented as a device connected to other equipment.

Figure 2:
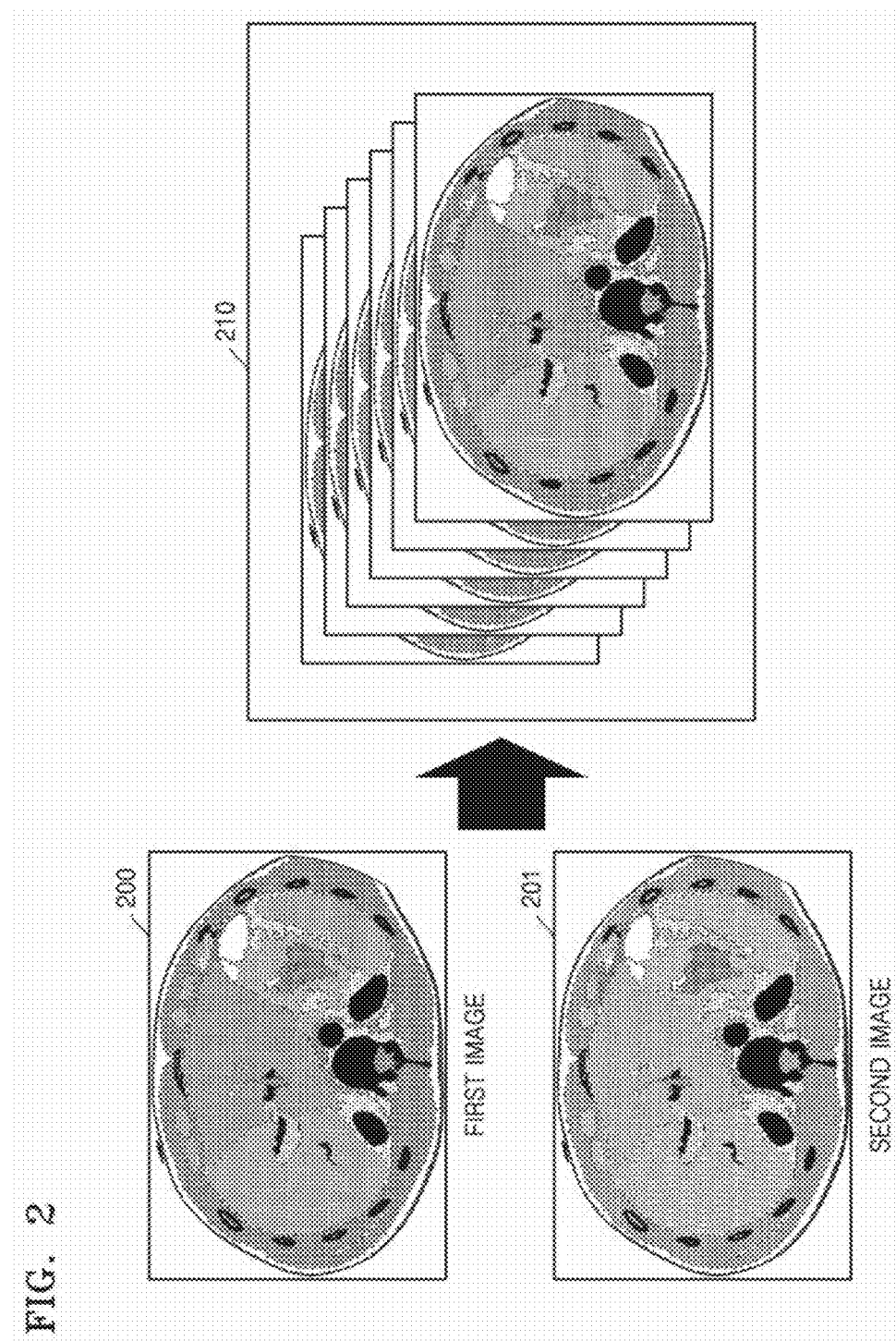
FIG. 2 is a diagram illustrating a process of obtaining a plurality of monochromatic images respectively corresponding to a plurality of energy levels, according to an embodiment.

FIG. 2 is a diagram illustrating a process of obtaining a plurality of monochromatic images respectively corresponding to a plurality of energy levels according to an embodiment.

Brightness expressed in a Hounsfield unit (HU) in a CT image may vary according to a linear attenuation coefficient of a material through which an X-ray passes. The linear attenuation coefficient may vary according to constituent components of the material and an energy level of a photon constituting the X-ray. Therefore, even though a first material and a second material in an object are different from each other, values of linear attenuation coefficient may be similar to each other at a specific energy level. Then, since the first material and the second material are expressed with similar brightness on an image, it may be difficult for a user to distinguish the first material from the second material in the CT image. In this case, the user may compare monochromatic images corresponding to different energy levels (e.g., 50 keV and 100 keV) to clearly distinguish different materials. A monochromatic image may be an image generated by irradiating an X-ray having a monochromatic energy level and performing CT on the object.

According to an embodiment, a CT image processing apparatus irradiates a polychromatic X-ray including photons having various energy levels to photograph the object. According to an embodiment, the CT image processing apparatus may obtain a virtual monochromatic image (VMI) corresponding to a plurality of energy levels from raw data obtained by irradiating the polychromatic X-ray and photographing the object. For example, the CT image processing apparatus may obtain first raw data and second raw data by irradiating the object with X-rays having two different energy spectra and performing CT on the object. For example, the CT image processing apparatus may obtain the first raw data and the second raw data by irradiating the object with an X-ray having tube voltages of 80 kVp and 140 kVp, but is not limited thereto. When the first raw data and the second raw data are obtained, the CT image processing apparatus may reconstruct the first raw data and the second raw data and obtain VMIs (for example, a first image 200 and a second image 201) corresponding to different energy levels.

Referring to FIG. 2, the CT image processing apparatus may obtain a plurality of VMIs 210 respectively corresponding to a plurality of energy levels, based on the first image 200 and the second image 201. For example, the CT image processing apparatus 100 may apply a virtual monochromatic imaging method to the first image 200 and the second image 201 to obtain the plurality of VMIs 210 respectively corresponding to the plurality of energy levels. For example, the CT image processing apparatus may obtain the plurality of VMIs 210 respectively corresponding to 20 energy levels sampled within an energy band less than or equal to 40 keV and equal to or greater than 140 keV. Here, the plurality of VMIs 210 may be VMIs respectively corresponding to a plurality of energy levels sampled at a 5 keV interval within the band less than or equal to 40 keV and equal to or greater than 140 keV.

According to another embodiment, the CT image processing apparatus may obtain a plurality of VMIs respectively corresponding to a plurality of energy levels, using a photon counting detector (PCD). For example, the CT image processing apparatus may detect a plurality of photons respectively for the plurality of energy levels to obtain the plurality of VMIs. According to a structure of the PCD, the photons of the plurality of energy levels may be detected by a plurality of photographing operations on the plurality of energy levels, or the photons of the plurality of energy levels may be detected by one photographing operation.

Figure 3:
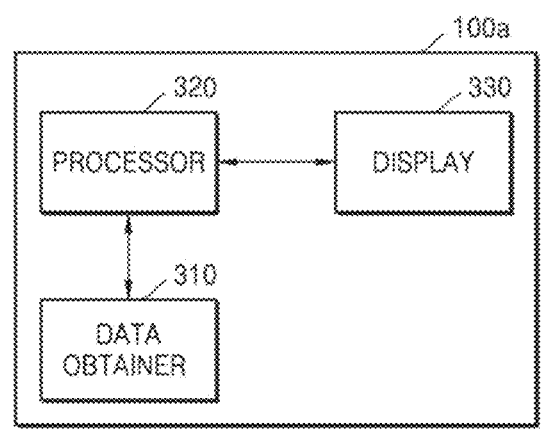
FIG. 3 is a block diagram showing a configuration of a CT image processing apparatus according to an embodiment.

FIG. 3 is a block diagram showing a configuration of a CT image processing apparatus 100a according to an embodiment.

The CT image processing apparatus 100a according to the embodiments is an apparatus for processing and displaying CT image data and may be implemented in the form of an electronic apparatus. For example, the CT image processing apparatus 100a may be implemented as various types of apparatuses including a processor and a display, such as a general-purpose computer, a tablet PC, a smart phone, and the like.

The CT image processing apparatus 100a according to the embodiments may be implemented as the CT system 100 shown in FIG. 1.

Referring to FIG. 3, the CT image processing apparatus 100a according to an embodiment may include a data obtainer 310, a processor 320, and a display 330. However, the CT image processing apparatus 100a may be implemented by more elements than the illustrated elements and is not limited to the above-described example.

Hereinafter, the element will be described in order.

The data obtainer 310 according to an embodiment may obtain raw data generated by performing CT photographing on an object. The raw data may be obtained in various manners, such as obtaining from a scanner of the CT image processing apparatus 100a, receiving from an external apparatus, or the like.

According to an embodiment, the data obtainer 310 may correspond to the scanner of the CT image processing apparatus 100a and may include, for example, the gantry 110 of the CT system 100 shown in FIG. 1. Accordingly, the data obtainer 310 may include a rotating frame 111, an X-ray generator 112, an X-ray detector 113, a rotation driver 114, and the readout device 115 shown in FIG. 1.

According to an embodiment, the data obtainer 310 may obtain first to third raw data by irradiating the object with an X-ray having a predetermined energy spectrum and performing CT photographing on the object. For example, the data obtainer 310 may irradiate the object with an X-ray having an energy spectrum of 0 keV to 140 keV and detect photons having a plurality of energy levels passing through the object. At this time, the data obtainer 310 may divide the plurality of energy levels into three ranges and may detect photons having the energy levels respectively corresponding to the ranges. For example, the data obtainer 310 may divide an energy level equal to or greater than 0 keV and less than 50 keV as a low energy range, an energy level equal to or greater than 50 keV and less than 100 keV as a middle energy range, and an energy level equal to or greater than 100 keV and less than or equal to 140 keV as a high energy range, but is not limited thereto. Accordingly, the data obtainer 310 may obtain first raw data, second raw data, and third raw data respectively corresponding to the low energy range, the middle energy range, and the high energy range.

The processor 320 performs predetermined processing based on a received user input. The processor 320 may be implemented in various combinations of one or more memories and one or more processors. For example, a memory may generate and delete a program module according to an operation of the processor 320 and the processor 320 may process operations of the program module.

The processor 320 according to an embodiment may reconstruct the first raw data to the third raw data to generate a first image to a third image, respectively. Also, the processor 320 may generate a plurality of VMIs respectively corresponding to a plurality of energy levels by calculating a weighted average of the generated first to third images. Thus, the user may more accurately diagnose a lesion using the plurality of generated VMIs.

The display 330 according to an embodiment may display a CT image obtained by performing CT photographing on the object.

When the display 330 is implemented as a touch screen, the display 330 may be used as an input device in addition to an output device. The display 330 may be implemented as, for example, a liquid crystal display, a thin film transistor-liquid crystal display, an organic light-emitting diode, a flexible display, a 3D display, an electrophoretic display, or the like. Also, according to an implementation form of the CT image processing apparatus 100a, the CT image processing apparatus 100a may include two or more displays 330.

The display 330 according to an embodiment displays the CT image generated by the processor 320.

Figure 4:
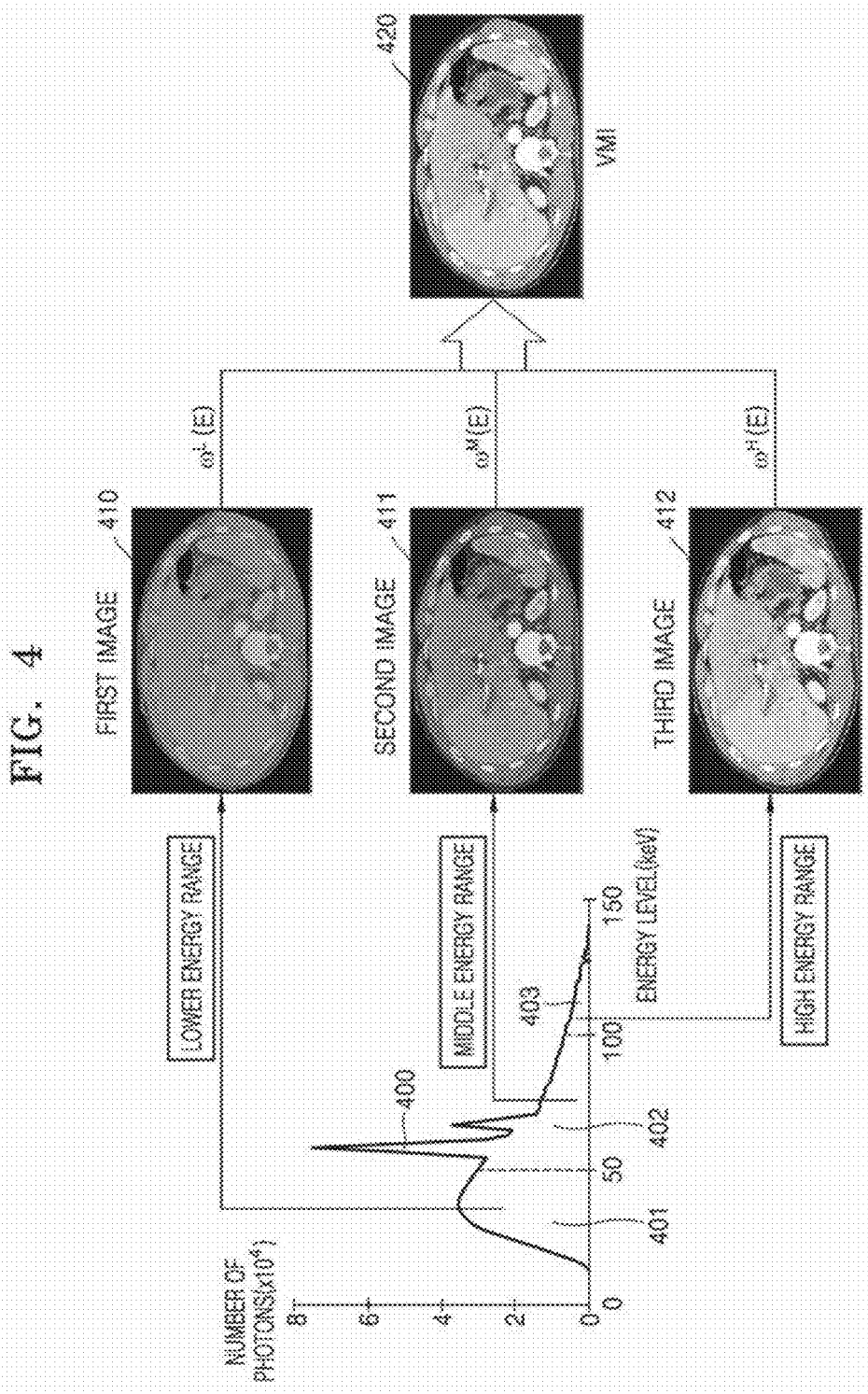
FIG. 4 is a diagram for explaining a method of obtaining virtual monochromatic image energy, according to an embodiment.

FIG. 4 is a diagram for explaining a method of obtaining virtual monochromatic image energy according to an embodiment.

Referring to FIG. 4, the CT image processing apparatus 100a according to an embodiment may irradiate an object with an X-ray having a predetermined energy spectrum 400 and detect photons having a plurality of energy levels. At this time, the CT image processing apparatus 100 may divide the plurality of energy levels into three or more energy ranges 401, 402, and 403 and detect the photons respectively corresponding to the energy ranges 401, 402, and 403. For example, the plurality of energy levels may be divided into a low energy range 401, a middle energy range 402, and a high energy range 403 but is not limited thereto. The CT image processing apparatus 100a may divide and detect the photons respectively corresponding to the low energy range 401, the middle range 402 and the high energy range 403 using a PCD. For example, the CT image processing apparatus 100*a* may divide an energy range equal to or greater than 0 keV and less than 50 keV as the I low energy range 401, an energy range equal to or greater than 50 keV and less than 100 keV as the middle range 402, and an energy range equal to greater than 100 keV and less than 140 keV as the high energy range 403 and divide and detect the photons respectively included in the low energy range 401, the middle range 402 and the high energy range 403, but is not limited thereto.

The CT image processing apparatus 100*a* according to an embodiment may obtain first data, second data, and third data by dividing and detecting the photons included in the three energy ranges 401, 402, and 403. The CT image processing apparatus 100*a* may obtain a first image to a third image 410, 411, and 412 corresponding to the three energy ranges 401, 402, and 403 by reconstructing the first to third raw data, respectively.

The CT image processing apparatus 100*a* according to an embodiment may obtain a VMI 420 corresponding to a specific energy level based on first to third images 410 to 412. For example, the CT image processing apparatus 100*a* may calculate a weighted average of the first to third images 410, 411, and 412 as follows to obtain the VMI 420.

$$I(E) = \omega^L(E)I^L + \omega^M(E)I^M + \omega^H(E)I^H, \qquad \text{[Equation 1]}$$

Referring to Equation 1, $I^L$, $I^M$, $I^H$ may denote the first image 410, the second image 411, and the third image 412, respectively. Weights applied to the first to third images 410, 411 and 412 may be expressed as a weighted function $\omega^L(E)$, $\omega^M(E)$, $\omega^H(E)$ with respect to the low energy range 401, the middle range 402 and the high energy range 403, respectively. At this time, $\omega^L(E)$, $\omega^M(E)$, $\omega^H(E)$ may be determined by the following Equations 2 to 4.

$\mu_3^H$ may respectively denote a linear attenuation coefficient of the first base material, the second base material, and the third base material in the high energy range 403.

The first base material to the third base material may mean materials having a relatively high proportion among materials constituting the object. For example, the first to third base materials may include, but are not limited to, water, bone, iodine, etc. It is difficult to set a weighted function with respect to the low energy range to the high energy range 401, 402, and 403 in consideration of all the materials constituting the object. Therefore, the prediction accuracy of the weighted function $\omega^L(E)$, $\omega^M(E)$, $\omega^H(E)$ may be improved by setting the weighted function in consideration of the first base material to the third base material having the relatively high proportion among the materials constituting the object.

The theoretical linear attenuation coefficient $\mu_1(E)$, $\mu_1(E)$, $\mu_1(E)$ of the first to third base materials may mean theoretically representing the linear attenuation coefficient of the first to third base materials at each energy level.

Unlike this, the linear attenuation coefficient $\mu_1^L$, $\mu_2^L$, $\mu_3^L$ of the first to third base materials in the low energy range 401, the linear attenuation coefficient $\mu_1^M$, $\mu_2^M$, $\mu_3^M$ of the first to third base materials in the medium energy range 402, and the linear attenuation coefficient $\mu_1^H$, $\mu_2^H$, $\mu_3^H$ of the first to third base materials in the high energy range 403 may mean values measured for the CT image processing apparatus 100*a* by irradiating the object with an X-ray and performing CT photographing on the object. $\mu_1^L$, $\mu_2^L$, $\mu_3^L$, $\mu_1^M$, $\mu_2^M$, $\mu_3^M$, $\mu_1^H$, $\mu_2^H$, $\mu_3^H$ may mean respectively weighted averages of the linear attenuation coefficients of the first to third base materials in each energy range, and weights of the linear attenuation coefficients may not be the same in each energy level. For example, a degree of attenuation may be different according to energy levels of photons

[Equation 2]
$$\omega(E)^L = \frac{(\mu_2(E)\mu_1^H - \mu_1(E)\mu_2^H)(\mu_3^H\mu_1^M - \mu_1^H\mu_3^M) + (\mu_3(E)\mu_1^H - \mu_1(E)\mu_3^H)(\mu_1^H\mu_2^M - \mu_2^H\mu_1^M)}{(\mu_1^H\mu_2^M - \mu_2^H\mu_1^M)(\mu_1^H\mu_3^L - \mu_3^H\mu_1^L) - (\mu_3^H\mu_1^M - \mu_1^H\mu_3^M)(\mu_2^H\mu_1^L - \mu_1^H\mu_2^L)} \times \frac{\mu_1^L}{\mu_1(E)},$$

[Equation 3]
$$\omega(E)^M = \frac{(\mu_2(E)\mu_1^H - \mu_1(E)\mu_2^H)(\mu_1^H\mu_3^L - \mu_3^H\mu_1^L) + (\mu_3(E)\mu_1^H - \mu_1(E)\mu_3^H)(\mu_2^H\mu_1^L - \mu_1^H\mu_2^L)}{(\mu_1^H\mu_2^M - \mu_2^H\mu_1^M)(\mu_1^H\mu_3^L - \mu_3^H\mu_1^L) - (\mu_3^H\mu_1^M - \mu_1^H\mu_3^M)(\mu_2^H\mu_1^L - \mu_1^H\mu_2^L)} \times \frac{\mu_1^M}{\mu_1(E)},$$

$$\omega(E)^H = 1 - \omega(E)^L - \omega(E)^M \qquad \text{[Equation 4]}$$

The weighted function $\omega^L(E)$, $\omega^M(E)$, $\omega^H(E)$ with respect to the low energy range to the high energy range 401, 402, and 403 may vary according to a linear attenuation coefficient of the object through which an X-ray passes in each energy range. The linear attenuation coefficient may vary according to a material of the object through which the X-ray passes and energy levels of photons constituting the X-ray.

Referring to Equations 2 to 4, $\mu_1(E)$, $\mu_1(E)$, $\mu_1(E)$ may respectively denote a theoretical linear attenuation coefficient of a first base material, a second base material, and a third base material constituting the object, $\mu_1^L$, $\mu_2^L$, $\mu_3^L$ may respectively denote a linear attenuation coefficient of the first base material, the second base material, and the third base material in the low energy range 401, $\mu_1^M$, $\mu_2^M$, $\mu_3^M$ may respectively denote a linear attenuation coefficient of the first base material, the second base material, and the third base material in the medium energy range 402, and $\mu_1^H$, $\mu_2^H$, detected by the X-ray detector 113 (e.g. the PCD) of the CT image processing apparatus 100*a* and according to a type of the X-ray detector 113.

The CT image processing apparatus 100*a* according to an embodiment may calculate a weighted average of the first to third images 410, 411 and 412 to obtain the VMI 420 corresponding to a specific energy level. Accordingly, the user may determine a lesion more accurately by using the VMI 420.

Figure 5:
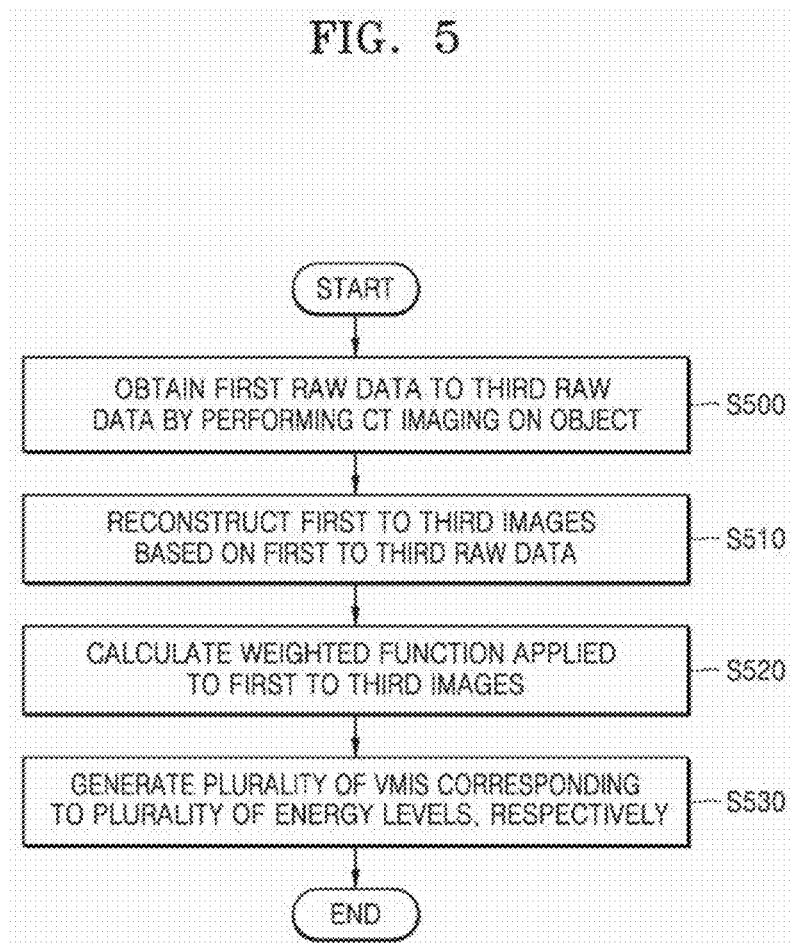
FIG. 5 is a flowchart illustrating a CT image processing method according to an embodiment.

FIG. 5 is a flowchart illustrating a CT image processing method according to an embodiment.

In operation S500, the CT image processing apparatus 100 may obtain first raw data to third raw data by irradiating an object with an X-ray having a predetermined energy spectrum (for example, 0 keV to 140 keV) and performing CT photographing on the object.

In operation S510, the CT image processing apparatus 100 may reconstruct the first to third raw data to generate first to third images respectively.

In operation S520, the CT image processing apparatus 100 may calculate a weighted function applied to the first to third images.

In operation S530, the CT image processing apparatus 100 may generate a plurality of VMIs corresponding to a plurality of energy levels, respectively, by calculating a weighted average of the generated first to third images.

Figure 6:
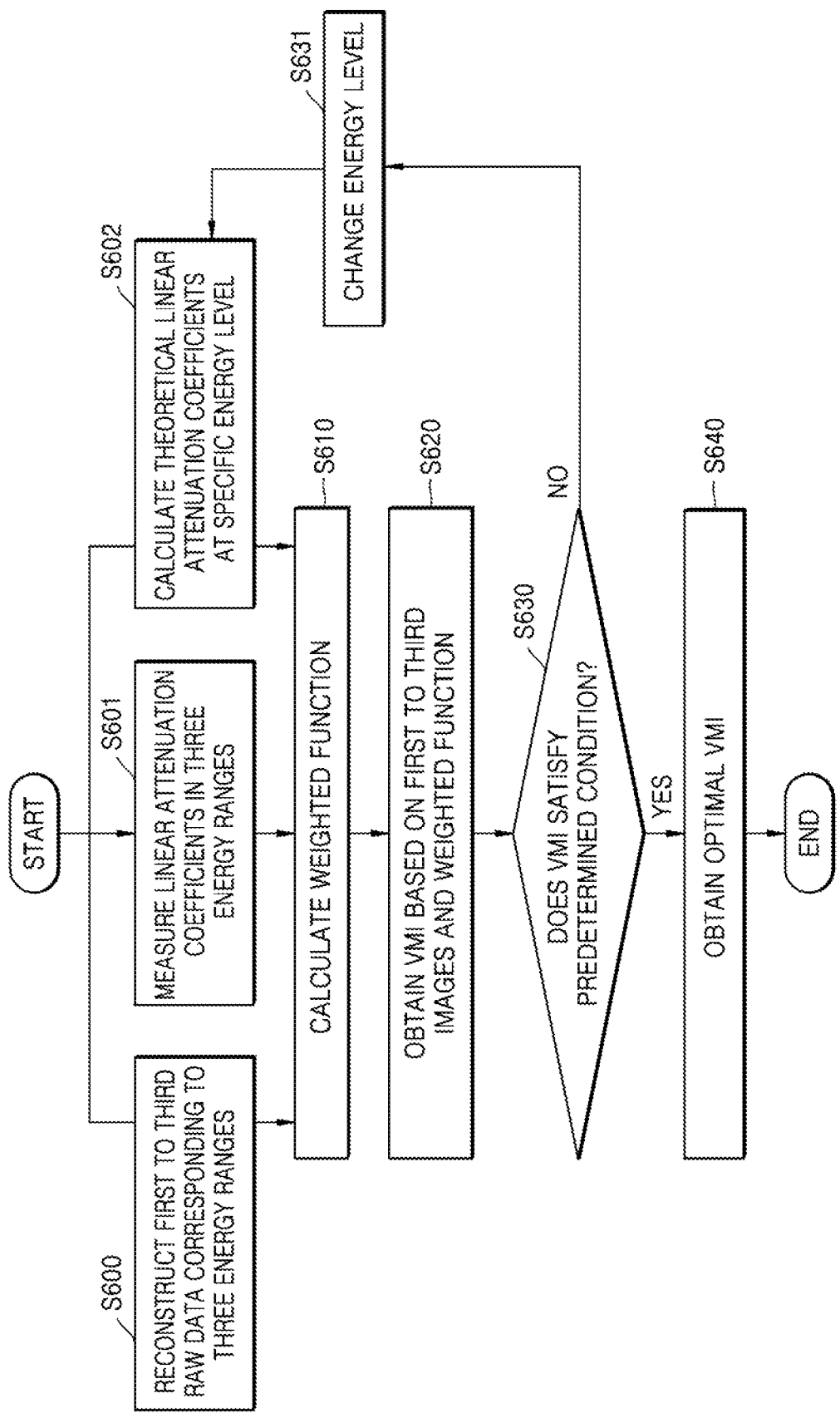
FIG. 6 is a flowchart illustrating a CT image processing method according to another embodiment.

FIG. 6 is a flowchart illustrating a CT image processing method according to another embodiment.

In operation S600, the CT image processing apparatus 100 may reconstruct first to third raw data corresponding to three different energy ranges and obtain first to third images.

In operation S601, the CT image processing apparatus 100 may obtain information about linear attenuation coefficients $\mu_1^L, \mu_2^L, \mu_3^L, \mu_1^M, \mu_2^M, \mu_3^M, \mu_1^H, \mu_2^H, \mu_3^H$ of first to third base materials in the three energy ranges. For example, the CT image processing apparatus 100 may irradiate an X-ray to an object and perform CT photographing on the object and measure the linear attenuation coefficients $\mu_1^L, \mu_2^L, \mu_3^L, \mu_1^M, \mu_2^M, \mu_3^M, \mu_1^H, \mu_2^H, \mu_3^H$ of the first base material to the third base material in the three different energy ranges respectively. At this time, $\mu_1^L, \mu_2^L, \mu_3^L, \mu_1^M, \mu_2^M, \mu_3^M, \mu_1^H, \mu_2^H, \mu_3^H$ represent the linear attenuation coefficients in one energy range including a plurality of energy levels, rather than linear attenuation coefficients at a monochromatic energy level. Thus, $\mu_1^L, \mu_2^L, \mu_3^L, \mu_1^M, \mu_2^M, \mu_3^M, \mu_1^H, \mu_2^H, \mu_3^H$ may mean a value obtained by calculating a weighted average of the linear attenuation coefficients at the plurality of energy levels included in the respective energy levels. However, in $\mu_1^L, \mu_2^L, \mu_3^L, \mu_1^M, \mu_2^M, \mu_3^M, \mu_1^H, \mu_2^H, \mu_3^H$ weights of the linear attenuation coefficients at the respective energy levels may differ from each other, and the linear attenuation coefficients at the respective energy levels may not be the same according to the CT image processing apparatus 100 or the X-ray detector 113 (e.g. a PCD) of the CT image processing apparatus 100. Therefore, the values of $\mu_1^L, \mu_2^L, \mu_3^L, \mu_1^M, \mu_2^M, \mu_3^M, \mu_1^H, \mu_2^H, \mu_3^H$ actually measured by irradiating the X-ray to the object and performing CT photographing on the object may differ from values calculated from theoretical linear attenuation coefficients $\mu_1(E), \mu_1(E), \mu_1(E)$.

In operation S602, the CT image processing apparatus 100 may calculate the theoretical linear attenuation coefficients of the first to third base materials at a specific energy level. The specific energy level may be an energy level at which a user wants to identify a VMI among the plurality of energy levels and may be a predetermined energy level by the CT image processing apparatus 100. For example, the CT image processing apparatus 100 may calculate the theoretical linear attenuation coefficients of the first to third base materials at the specific energy level using $\mu_1(E), \mu_1(E), \mu_1(E)$ previously stored in a memory.

In operation S610, the CT image processing apparatus 100 may calculate a weighted function $\omega^L(E), \omega^M(E), \omega^H(E)$ using the linear attenuation coefficients obtained in operations S601 and S602.

In operation S620, the CT image processing apparatus 100 may obtain a VMI corresponding to a specific energy level by respectively apply $\omega^L(E), \omega^M(E), \omega^H(E)$ to the first to third images.

In operation S630, the CT image processing apparatus 100 may determine whether the obtained VMI satisfies a predetermined condition. For example, the CT image processing apparatus 100 may determine whether a contrast-to-noise ratio (CNR) of the obtained VMI is equal to or greater than a pre-determined value. Regions for comparing the CNR may be different according to a part of the object that the user is to observe. For example, when the VMI is obtained by injecting a contrast agent into a stroke patient and performing CT photographing on the brain of the stroke patient, the user may want to observe a region corresponding to the contrast agent in the VMI. At this time, the larger the CNR of the region corresponding to the contrast agent, the easier the user may read the image. As another example, when the VMI is obtained by performing CT photographing on a liver of a patient with cirrhosis, the user may want to observe a region corresponding to the liver in the VMI. At this time, the CT image processing apparatus 100 may determine whether a CNR of the region corresponding to the liver is equal to or greater than the pre-determined value, and when it is determined that the CNR is equal to or greater than the pre-determined value, and determine the obtained VMI as an optimal VMI (operation S640). However, the predetermined condition is not limited to the above-described example, and may include one or more conditions used for determining an image that that the user may easily read.

When the obtained VMI does not satisfy the predetermined condition, in operation S631, the CT image processing apparatus 100 may change an energy level for obtaining the VMI. Then, the CT image processing apparatus 100 may respectively calculate theoretical linear attenuation coefficients of the first base material to the third base material at the changed energy level. When the obtained VMI does not satisfy the predetermined condition, the CT image processing apparatus 100 may obtain a VMI corresponding to the changed energy level, determine whether the VMI corresponding to the changed energy level satisfies the predetermined condition, and automatically determine the VMI.

According to an embodiment, a reference for changing the energy level may differ according to a region of the object on which CT photographing is performed. For example, an energy level at which a CNR appears relatively large may be different according to a region (e.g., brain, abdomen, lung, etc.) of the object on which CT photographing is performed. Also, the energy level at which the CNR appears relatively large may vary according to an internal structure (e.g., blood vessel, soft tissue, etc.) of the object to be observed by the user. When the obtained VMI does not satisfy the predetermined condition, the CT image processing apparatus 100 may change the energy level to the energy level at which the CNR appears relatively large in the region of the object on which CT photographing is performed and/or the internal structure of the object to be observed by the user and obtain the VMI corresponding to the changed energy level again.

The CT image processing apparatus 100 according to the embodiment may obtain the VMI corresponding to the changed energy level while changing the energy level until the VMI satisfying the predetermined condition is obtained. Accordingly, the CT image processing apparatus 100 may automatically determine the energy level that the user may easily read the image, without having to manually select a specific energy level to be observed by the user.

Figure 7:
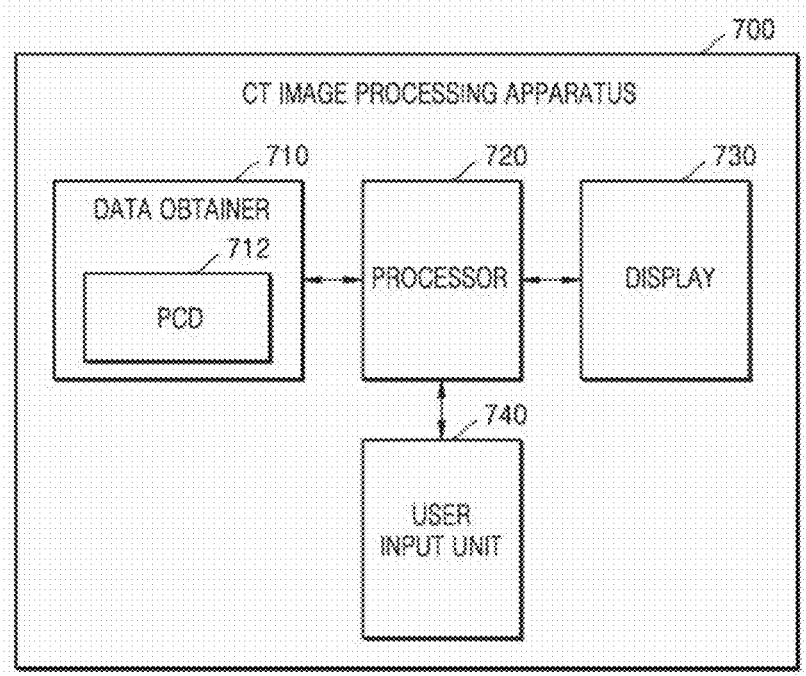
FIG. 7 is a block diagram showing a configuration of a CT image processing apparatus according to an embodiment.

FIG. 7 is a block diagram showing a configuration of a CT image processing apparatus 700 according to an embodiment.

Referring to FIG. 7, the CT image processing apparatus 700 may include a data obtainer 710, a processor 720, a display 730, and a user input unit 740. However, the CT image processing apparatus 700 may be implemented by more elements than the illustrated elements, and is not limited to the example described above.

The data obtainer 710, the processor 720 and the display 730, which are the elements included in the CT image processing apparatus 700, are respectively the same as the data obtainer 310, the processor 320 and the display 330 of the CT image processing apparatus 100a shown in FIG. 3, and thus redundant descriptions thereof will be omitted, and only distinguished technical features will be described.

The CT image processing apparatus 700 shown in FIG. 7 is an apparatus for processing and displaying CT image data and may be implemented in the form of an electronic apparatus. For example, the CT image processing apparatus 700 may be implemented as various types of apparatuses including a processor and a display, such as a general-purpose computer, a tablet PC, a smart phone, and the like.

The data obtainer 710 may detect X-rays having different energy spectra transmitted through an object and obtain raw data in each energy range through the detected X-rays. The raw data may be obtained in various manners, such as obtaining from a scanner of the CT image processing apparatus 700, receiving from an external apparatus, or the like.

According to an embodiment, the data obtainer 710 may irradiate the object with an X-ray having an energy spectrum of 0 keV to 140 keV, and may include a PCD 712 that detects photons having a plurality of energy levels transmitted through the object. The PCD 712 may divide the energy spectrum corresponding to 0 keV to 140 keV into three energy ranges and divide and detect the photons having the energy levels respectively corresponding to the three energy ranges. For example, the PCD 712 may divide an energy level equal to or greater than 0 keV and less than 50 keV as a low energy range, an energy level equal to or greater than 50 keV and less than 100 keV as a middle energy range, and an energy level equal to or greater than 100 keV and less than or equal to 140 keV as a high energy range, but is not limited thereto.

The data obtainer 710 may obtain first raw data, second raw data, and third raw data corresponding to the low energy range, the middle energy range, and the high energy range, respectively.

The processor 720 may be implemented in various combinations of one or more memories and one or more processors. The processor 720 may be implemented as a hardware module including at least one of, for example, a central processing unit, a microprocessor, a graphic processing unit, a random-access memory (RAM), or a read-only memory. In an embodiment, the processor 720 may be implemented as an application processor (AP).

The processor 720 may generate a CT image by reconstructing the raw data transmitted from the data obtainer 710. In an embodiment, the processor 720 may reconstruct the first to third raw data, respectively, to generate a first CT image to a third CT image. The processor 720 may calculate a weighted function applied to each of the first to third images and generate a plurality of VMIs respectively corresponding to a plurality of energy levels by calculating a weighted average of the first to third images.

The processor 720 may set a region of interest (ROI) on the CT image based on a user input received via the user input unit 740. In an embodiment, the processor 720 may set blood vessels, tissues, and background areas on the CT image as ROI based on the user input.

The processor 720 may determine a CNR of the ROI and may determine a VMI of an energy level at which the determined CNR is the maximum among the plurality of VMIs.

In an embodiment, the processor 720 may determine an image of an energy level at which the determined CNR is equal to or greater than a predetermined value as the VMI among the plurality of VMIs. In an embodiment, when there is a plurality of images of the energy level at which the determined CNR is equal to or greater than the predetermined value, the processor 720 may determine any one of the plurality of images as the VMI.

The processor 720 according to an embodiment may determine a concentration of a contrast agent injected into the object in the ROI and determine the energy level at which the determined CNR is the maximum based on a type of the contrast agent input through the user input unit 740 and a relationship between the measured concentration of the contrast agent and the CNR. In this case, the CT image processing apparatus 700 further include a memory that stores information about the type of the contrast agent and the relationship between the measured concentration and the CNR in the form of a look-up table (LUT) as an element. The processor 720 may determine the VMI of the energy level at which the measured CNR is the maximum according to the concentration of the contrast agent measured in the ROI and the type of the contrast agent with reference to the LUT stored in the memory. This will be described in detail in FIGS. 11 and 12.

The processor 720 according to an embodiment may measure a size of the object in the CT image and determine the VMI of the energy level at which the measured CNR is the maximum based on the measured size of the object. In this case, the CT image processing apparatus 700 may further include a memory that stores CNR information according to the size of the object in the form of a LUT as an element. The processor 720 may determine the VMI of the energy level at which the measured CNR is the maximum according to the measured size of the object with reference to the LUT stored in the memory. This will be described in detail with reference to FIGS. 13 to 15.

The processor 720 according to an embodiment may obtain identification information of a patient who is a target of CT photographing and determine the VMI of the energy level at which the measured CNR is the maximum according to the obtained identification information of the patient. In this case, the processor 720 may further include a memory that stores information about the energy level at which the measured CNR is the maximum according to information about a previously examined patient as an element, and determine the VMI of the energy level at which the measured CNR is the maximum according to the information about the patient stored in the memory. This will be described in detail with reference to FIG. 16.

The user input unit 740 may receive a user input to set a ROI on the CT image. The user input unit 740 according to an embodiment may receive a user input to designate blood vessels, tissue, and a background region on the CT image as the ROI, but is not limited thereto. The user input unit 740 may set at least one of blood vessels, tissue, and background region on the CT image as the ROI.

The user input unit 740 according to an embodiment may receive a user input to input information about the type of the contrast agent injected into the object.

The user input unit 740 may include, but is not limited to, a hardware configuration such as a key pad, a mouse, a trackball, a touch pad, a touch screen, and a jog switch, etc.

Figure 8:
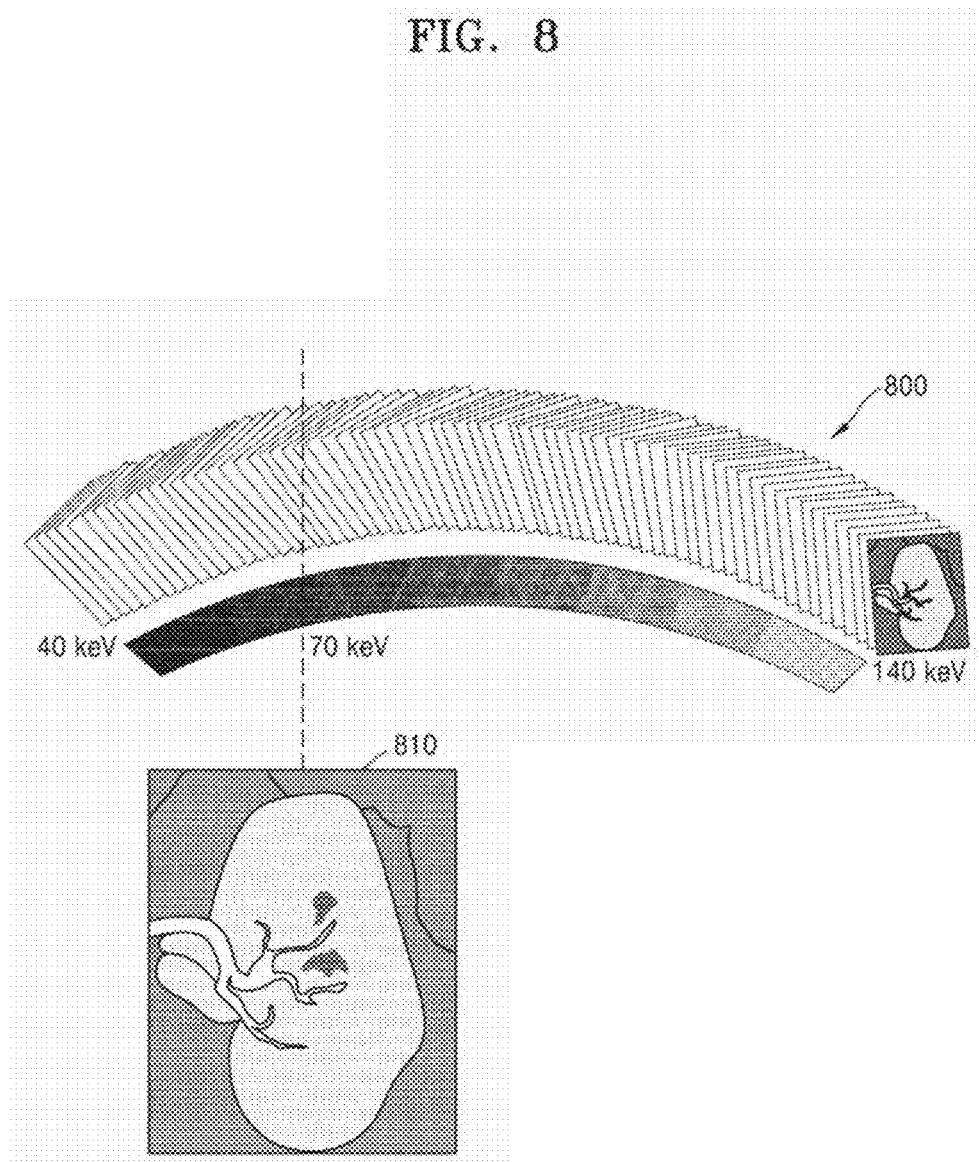
FIG. 8 is a diagram for explaining a method of obtaining a plurality of monochromatic images corresponding to a plurality of energy levels, respectively, the method being performed by a CT image processing apparatus, according to an embodiment.

FIG. 8 is a diagram for explaining a method performed by the CT image processing apparatus 700 of obtaining a plurality of VMIs 800 corresponding to a plurality of energy levels, respectively, according to an embodiment.

Referring to FIG. 8, the CT image processing apparatus 700 (see FIG. 7) may irradiate an object with a polychromatic X-ray including photons having various energy levels and detect the X-ray transmitted through the object to obtain a CT image.

The CT image processing apparatus 700 may obtain VMIs respectively corresponding to the plurality of energy levels from raw data obtained by irradiating the object with the polychromatic X-ray and photographing the object. In an embodiment, the CT image processing apparatus 700 may divide the X-rays into three energy ranges through the PCD 712 (see FIG. 7), detect X-rays having different energy spectra transmitted through the object, amplify the detected X-rays, and obtain first raw data to third raw data. The CT image processing apparatus 700 may generate a first CT image to a third CT image by reconstructing the first raw data to the third raw data. The CT image processing apparatus 700 may calculate a weighted function applied to each of the first to third CT images and generate a plurality of VMIs 800 respectively corresponding to the plurality of energy levels by calculating the weighted average.

In the embodiment shown in FIG. 8, the CT image processing apparatus 700 may generate the plurality of VMIs 800 having energy levels equal to or greater than 40 keV and less than or equal to 140 keV. In an embodiment, the plurality of VMIs 800 may be VMIS respectively corresponding to 101 energy levels sampled at a 1 keV interval within an energy band equal to or greater than 40 keV and less than or equal to 140 keV.

The CT image processing apparatus 700 according to an embodiment may determine a CNR within a ROI and determined a VMI 800 of an energy level at which the CNR is maximum among the plurality of VMIs 800. In the embodiment of FIG. 8, the CT image processing apparatus 700 determine that a CNR of the VMI 810 of 70 keV is the highest among the plurality of VMIs 800 respectively corresponding to the 101 energy levels equal to or greater than 40 keV and less than or equal to 140 keV but this is merely an example, and is not necessarily limited to 70 keV.

The CT image processing apparatus 700 according to an embodiment may automatically determine the energy level at which the CNR is the maximum among the plurality of VMIs 800 and display the VMI 810 of the determined energy level.

However, the disclosure is not limited thereto and the CT image processing apparatus 700 according to an embodiment may determine an image of an energy level at which the CNR is equal to or greater than a predetermined value as the VMI 810 among the plurality of VMIs 800 and display the determined VMI 810.

The larger the CNR of the region into which the contrast agent is injected, the easier the user may read the image and the more accurate the diagnosis may be made. The spectral CT imaging according to the related art may not know an energy level at which the CNR is maximum according to the contrast agent among a plurality of VMIs having a plurality of energy levels, thus the user has to manually search for an image of a determined energy level keV, which is cumbersome and takes a long time.

The CT image processing apparatus 700 according to an embodiment shown in FIGS. 7 and 8 may automatically determine the energy level at which the CNR is the maximum among the plurality of VMIs 800 respectively corresponding to the plurality of energy levels, and display the VMI 810 of the determined energy level, thereby improving the user convenience and increasing the accuracy of diagnosis.

Figure 9:
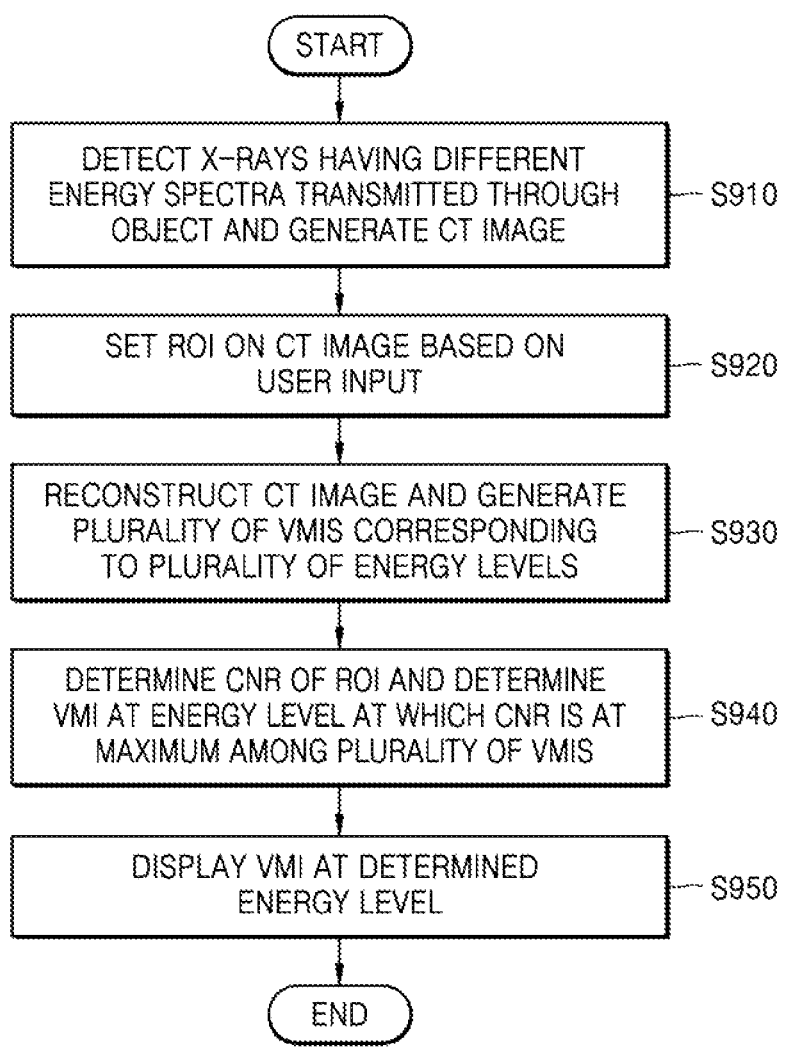
FIG. 9 is a flowchart illustrating a method of determining a VMI having a maximum contrast-to-noise ratio (CNR) and displaying the VMI, the method being performed by a CT image processing apparatus, according to an embodiment.

FIG. 9 is a flowchart illustrating a method performed by a CT image processing apparatus of determining a VMI having a maximum CNR and displaying the VMI according to an embodiment.

In operation S910, the CT image processing apparatus detects X-rays having different energy spectra transmitted through an object to generate a CT image. The CT image processing apparatus according to an embodiment may divide the X-rays having different energy spectra irradiated to the object into three energy ranges, amplify the detected X-rays, and obtain first raw data to third raw data. The CT image processing apparatus according to an embodiment may detect the X-rays using a PCD that detects photons having energy levels respectively corresponding to the three energy ranges and obtain the first raw data to the third raw data. The CT image processing apparatus may generate a first CT image to a third CT image by reconstructing the first raw data to the third raw data.

In operation S920, the CT image processing apparatus sets an ROI on the CT image based on a user input. The CT image processing apparatus according to an embodiment may receive the user input designating a blood vessel, tissue, and a background region on the CT image and set the blood vessel, tissue, and background region on the CT image based on the received user input as the ROI, but is not limited thereto. The CT image processing apparatus may set at least one of the blood vessel, tissue, lesion side, and background tissue as the ROI.

In operation S930, the CT image processing apparatus may generate a plurality of VMIs corresponding to a plurality of energy levels by reconstructing the CT image. The CT image processing apparatus according to an embodiment may calculate a weighted function applied to each of the first to third CT images generated in operation S910 and generate the plurality of VMIs corresponding to the plurality of energy levels by calculating a weighted average of the first to third CT images. The CT image processing apparatus according to an embodiment may generate a total of 101 VMIs sampled in units of 1 keV at energy levels equal to or greater than 40 keV and less than or equal to 140 keV, but is not limited thereto.

In operation S940, the CT image processing apparatus determines a CNR of the ROI and determines a VMI of an energy level at which the CNR is the maximum among the plurality of VMIs. The CT image processing apparatus according to an embodiment may determine a CNR of a region corresponding to the ROI in the plurality of VMIs respectively corresponding to the energy levels equal to or greater than 40 keV and less than or equal to 140 keV and determine the energy level at which the determined CNR is the maximum among the plurality of VMIs. The CT image processing apparatus may select a VMI of the energy level having the highest CNR.

In an embodiment, the CT image processing apparatus may determine an image of an energy level at which the CNR is greater than a predetermined value as the VMI among the plurality of VMIs.

In operation S950, the CT image processing apparatus displays the VMI at the determined energy level.

Figure 10:
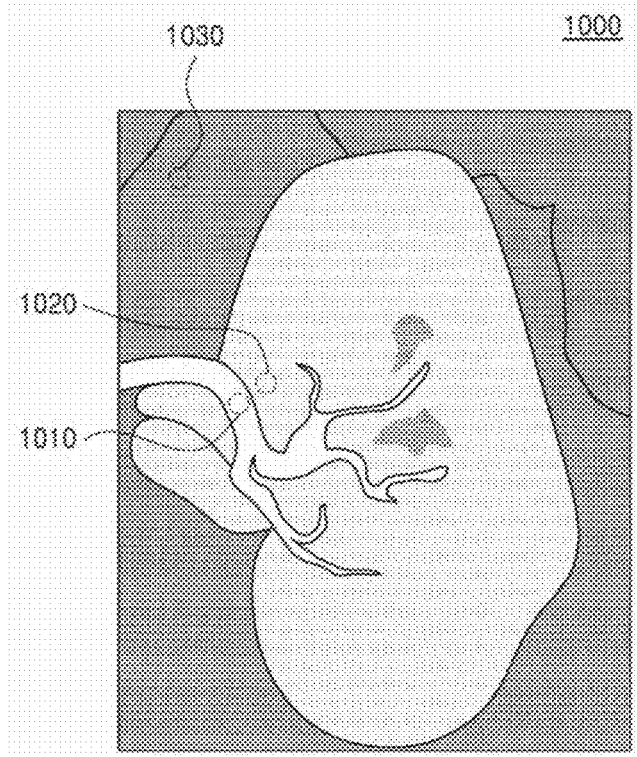
FIG. 10 is a diagram illustrating a method of setting an ROI on a CT image, the method being performed by a CT image processing apparatus, according to an embodiment.

FIG. 10 is a diagram illustrating a method performed by a CT image processing apparatus of setting a ROI on a CT image 1000 according to an embodiment.

Referring to FIG. 10, the CT image processing apparatus may receive a user input that sets a predetermined region of an object on the CT image 1000 as the ROI. The CT image processing apparatus according to an embodiment may receive the user input that sets one or more regions of a blood vessel 1010, a tissue 1020, and a background tissue 1030 on the CT image 1000 as ROIs.

The CT image processing apparatus may set one or more regions of the blood vessel 1010, the tissue 1020, and the background tissue 1030 on the CT image 1000 as ROIs based on the received user input. The CT image processing apparatus according to an embodiment may set two regions such as the blood vessel 1010 and the background tissue 1030 or the tissue 1020 and the background tissue 1030 as ROIs, but is not limited thereto. Here, the tissue 1020 may be a tissue in which a main lesion of a patient appears.

The CT image processing apparatus may calculate a CNR of the ROI based on Equation 5 shown below.

$$CNR = \left| \frac{\text{Mean}(\text{Target1}) - \text{Mean}(\text{Target2})}{\text{Std}(\text{background})} \right| \quad \text{[Equation 5]}$$

Referring to Equation 5, the CNR may be calculated by dividing a difference between an average value of a first region Target 1 and an average value of a second region Target 2 set as ROIs by a standard deviation of a background region. The CT image processing apparatus according to an embodiment may calculate the CNR of the ROIs by setting the blood vessel 1010 and the tissue 1020 as the first region Target 1 and the second region Target 2 respectively and dividing a difference between an average of HU values of the blood vessel 1010 and an average of HU values of the tissue 1020 by the standard deviation.

The CT image processing apparatus according to an embodiment may perform CNR calculation with respect to the ROI on a plurality of VMIs corresponding to a plurality of energy levels, respectively.

Figure 11:
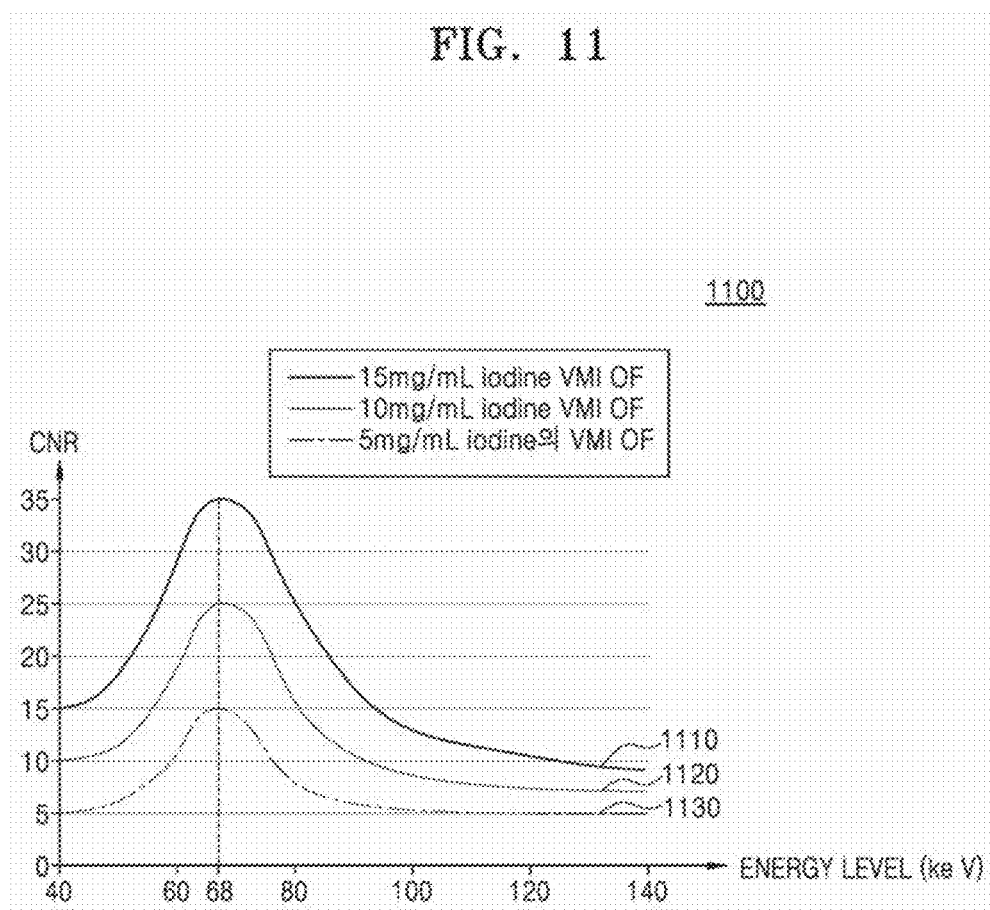
FIG. 11 is a graph showing a relationship between an energy level and a CNR, according to concentration of a contrast agent.

FIG. 11 is a graph 1100 showing a relationship between an energy level and a CNR according to concentration of a contrast agent.

Referring to FIG. 11, the graph 1100 shows the relationship of the CNR with the energy level (keV) according to the concentration of the contrast agent. In the embodiment shown in FIG. 11, iodine is used as the contrast agent, but a type of the contrast agent is not limited to iodine.

A first curve 1110 in the graph 1100 is a curve graph showing the CNR according to the energy level when the iodine contrast agent of 15 mg/mL is injected into an object. A second curve 1120 and a third curve 1130 are curve graphs showing the CNRs according to the energy levels when the iodine contrast agent of 10 mg/mL and 5 mg/mL are injected into the object, respectively.

Referring to the first curve 1110 to the third curve 1130, the relationship between the energy level and the CNR is in direct proportion at an energy level equal to or greater than 40 keV and less than or equal to 68 keV. At energy levels equal to or greater than 68 keV of the first curve 1110 to the third curve 1130, the larger the energy level is, the smaller the value of CNR is. The first to third curves 1110 to 1130 all have the maximum CNR at the energy level of 68 keV. However, this is only an example, and the energy level at which the CNR is maximum may vary according to the concentration of the contrast agent and the type of the contrast agent.

A CT image processing apparatus according to an embodiment may store information about the relationship between the CNR and the energy level based on the concentration of the contrast agent and the type of the contrast agent shown in the graph 1100. For example, the CT image processing apparatus may store the information about the relationship between the CNR and the energy level in a form of a LUT in an internal memory, but is not limited thereto. The CT image processing apparatus may store the information about the relationship between the CNR and the energy level in an external database. The CT image processing apparatus may determine an energy level at which the CNR is the maximum according to the concentration of the contrast agent and the type of the contrast agent with reference to the stored LUT and display a VMI of the determined energy level.

Figure 12:
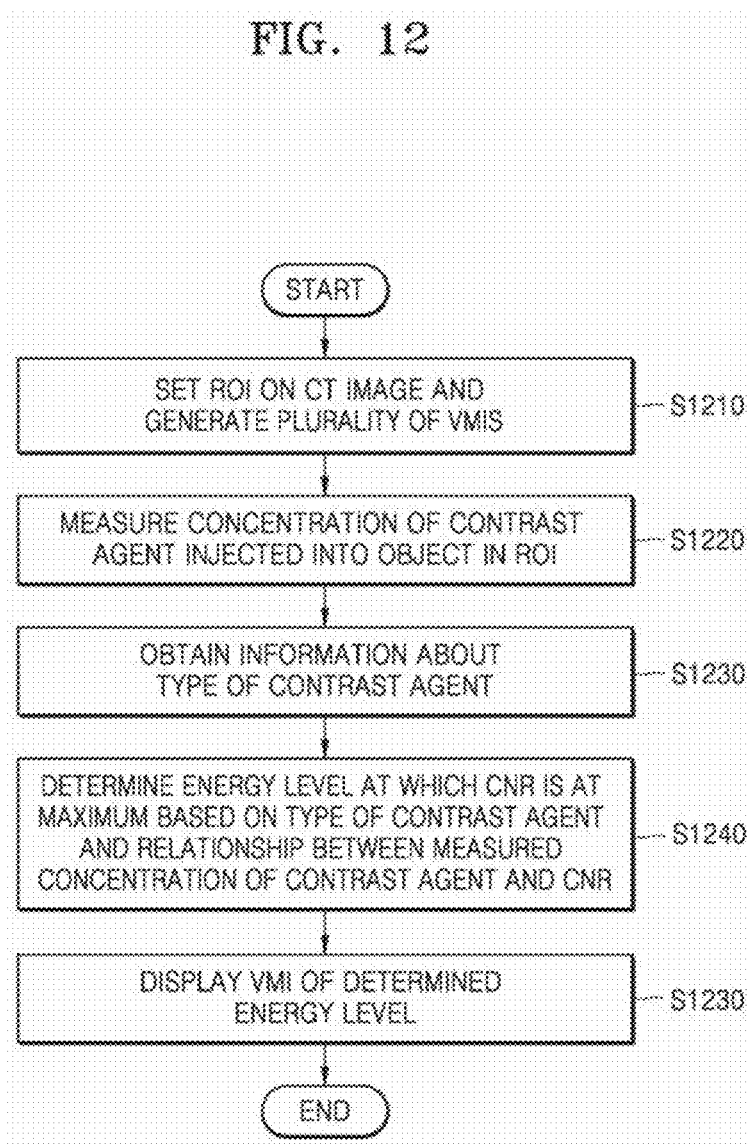
FIG. 12 is a flowchart showing a method of determining a VMI of an energy level at which a CNR is the maximum based on a concentration of a contrast agent and a type of the contrast agent, the method being performed by a CT image processing apparatus, according to an embodiment.

FIG. 12 is a flowchart showing a method performed by a CT image processing apparatus of determining a VMI of an energy level at which a CNR is the maximum based on a concentration of a contrast agent and a type of the contrast agent according to an embodiment.

In operation S1210, the CT image processing apparatus sets a ROI on a CT image and generates a plurality of VMIs. The CT image processing apparatus according to an embodiment may set one or more regions of blood vessels, tissues, and background tissues as ROIs on the CT image based on a received user input. The CT image processing apparatus according to an embodiment may generate the plurality of VMIs corresponding to a plurality of energy levels by reconstructing the CT image. A method of generating the plurality of VMIs is the same as operation S930 of FIG. 9, and thus a redundant description thereof will be omitted.

In operation S1220, the CT image processing apparatus measures the concentration of the contrast agent injected into an object in the ROI.

In operation S1230, the CT image processing apparatus obtains information about the type of the contrast agent. The CT image processing apparatus according to an embodiment may receive the information on the type of the contrast agent from a user. When photographing the CT image, the contrast agent injected into the object may be iodine, but is not limited thereto. The CT image processing apparatus may recognize the type of the contrast agent through contrast agent information input from the user.

In operation S1240, the CT image processing apparatus determines the energy level at which the CNR is the maximum based on the type of the contrast agent and a relationship between the measured concentration of the contrast agent and the CNR. The CT image processing apparatus according to an embodiment may include a memory that stores information about the relationship between the CNR and the energy level according to the type and the concentration of the contrast agent in the form of a LUT, but is not limited thereto, and the CT image processing apparatus may store the information about the relationship between the CNR and the energy level according to the type and the concentration of the contrast agent in an external database. The CT image processing apparatus according to an embodiment may determine the energy level at which the CNR is the maximum according to the concentration of the contrast agent measured in operation S1220 and the type of the contrast agent obtained in operation S1230 with reference to the LUT stored in the memory.

The CT image processing apparatus according to an embodiment may determine an image of an energy level at which the CNR is greater than a predetermined value as the VMI among the plurality of VMIs based on the relationship between the CNR and the energy level according to the type and the concentration of the contrast agent.

In operation S1250, the CT image processing apparatus displays the VMI of the determined energy level.

Figure 13:
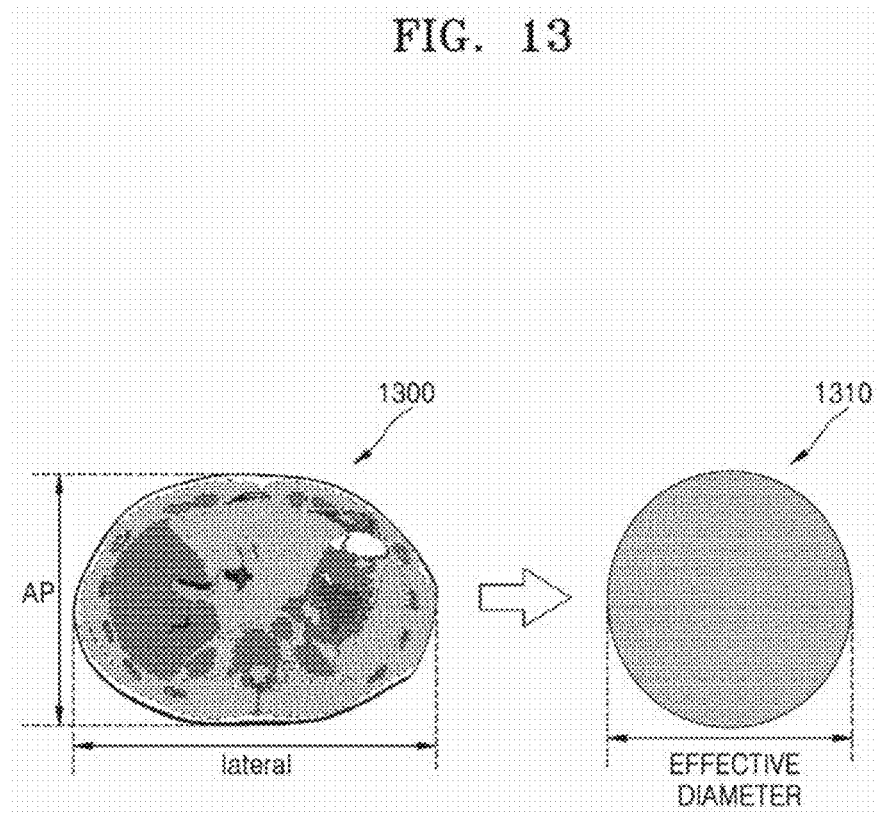
FIG. 13 is a diagram for explaining a method of measuring a size of an object, the method being performed by a CT image processing apparatus, according to an embodiment.

FIG. 13 is a diagram for explaining a method performed by a CT image processing apparatus of measuring size of an object according to an embodiment.

Referring to FIG. 13, the CT image processing apparatus may measure the size of the object in a CT image 1300 obtained by performing CT photographing on the object. In the embodiment of FIG. 13, the CT image 1300 is obtained by photographing the abdomen of a person. The abdomen in the CT image 1300 may have a predetermined size in a front-back direction AP and a lateral direction.

The CT image processing apparatus according to an embodiment may estimate a phantom 1310 having the same size as the object in the CT image 1300 and measure the size of the object according to an effective diameter of the phantom 1310. In an embodiment, the CT image processing apparatus may measure the size of the object through the effective diameter of a water phantom having the same size of the object in the CT image 1300. However, the phantom 1310 is not limited to the water phantom.

Figure 14:
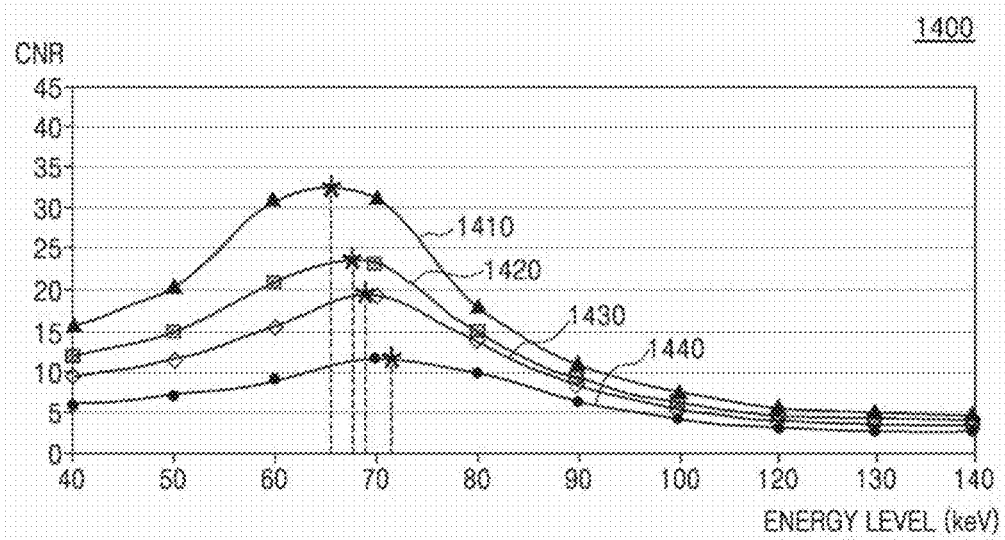
FIG. 14 is a graph showing a relationship between an energy level and a CNR, according to a size of an object.

FIG. 14 is a graph 1400 showing relationship between an energy level and a CNR according to size of an object.

Referring to FIG. 14, the graph 1400 shows the relationship of the CNR according to the energy level keV with respect to the size of the object. The CNR may vary according to the size of the object measured on a CT image, and an energy level at which the CNR is the maximum may also vary according to the size of the object. Here, the size of the object on the CT image may be obtained through an effective diameter of a phantom, but is not limited thereto. In an embodiment, the phantom may be, but is not limited to, a water phantom.

In the graph 1400, a first curve 1410 is a curve graph showing a CNR according to an energy level when the size of the object measured in the CT image is a first size. A second curve 1420, a third curve 1430, and a fourth curve 1440 are curve graphs showing the CNRs according to energy levels when the sizes of the object measured on the CT image are a second size, a third size, and a fourth size, respectively.

Referring to the first curve 1410 in the graph 1400 shown in FIG. 14, the relationship between the energy level and the CNR is in direct proportion at an energy level equal to or greater than 40 keV and less than or equal to 65 keV. In the first curve 1410, the energy level with the maximum CNR may be determined to be equal to or greater than 65 keV. In the first curve 1110, the maximum CNR may be measured at the energy level of about 65 keV. The maximum CNR may be determined at about 68 keV in the second curve 1420, about 69 keV in the third curve 1430, and about 71 keV in the fourth curve 1440.

The CT image processing apparatus according to an embodiment may store information about the relationship between the CNR and the energy level according to the size of the object on the CT image shown in the graph 1400. For example, the CT image processing apparatus may store the information about the relationship between the CNR and the energy level according to the size of the object in a form of a LUT in an internal memory, but is not limited thereto. The CT image processing apparatus may store the information about the relationship between the CNR and the energy level according to the size of the object in an external database. The CT image processing apparatus may determine an energy level at which the CNR is the maximum according to the size of the object in the CT image measured through the phantom with reference to the previously stored LUT and display a VMI at the determined energy level.

The CT image processing apparatus according to an embodiment may determine an image of an energy level at which the CNR is greater than a predetermined value as the VMI among the plurality of VMIs based on the size of the object and the information about the relationship between the CNR and the energy level.

FIG. 15 is a flowchart showing a method performed by a CT image processing apparatus of determining a VMI of an energy level at which a CNR is the maximum based on size of an object according to an embodiment.

In operation S1510, the CT image processing apparatus generates a plurality of VMIs by reconstructing a CT image. A method of generating the plurality of VMIs is the same as operation S930 of FIG. 9, and thus a redundant description thereof will be omitted.

In operation S1520, the CT image processing apparatus measures the size of the object in the CT image. The CT image processing apparatus according to an embodiment may measure the size of the object in the CT image through sizes of various phantom having diameters of different sizes. In an embodiment, the CT image processing apparatus may estimate a water phantom having the same size as the object in the CT image and measure the size of the object through an effective diameter of the water phantom. For example, the CT image processing apparatus may measure the size of the object according to the effective diameter of the water phantom, assuming the water phantom having approximately the same size as the object in the front-back direction AP and the lateral direction. However, a method of measuring the size of the object using the water phantom is only an embodiment, and a type of the phantom is not necessarily limited to the water phantom.

In operation S1530, the CT image processing apparatus determines the energy level at which the CNR is the maximum based on information about a relationship between the measured size of the object and the CNR. The CT processing apparatus according to an embodiment may include a memory that stores information about relationship between the energy level and the CNR according to the size of the object in the form of a LUT as an element and determine the energy level at which the CNR is the maximum according to the measured size of the object, but is not limited thereto.

The CT image processing apparatus may store the information about the relationship between the energy level and the CNR according to the size of the object in an external database. In this case, the CT image processing apparatus may access the database to obtain the information about the relationship between the energy level and the CNR according to the size of the object and determine the energy level at which the CNR is the maximum according to the size of the object measured in the CT image with reference to the obtained information.

The CT image processing apparatus according to an embodiment may determine an image of an energy level at which the CNR is greater than a predetermined value as the VMI among the plurality of VMIs based on the size of the object and the relationship between the CNR and the energy level.

In operation S1540, the CT image processing apparatus displays the VMI of the determined energy level.

FIG. 16 is a flowchart showing a method performed by a CT image processing apparatus of determining a VMI of an energy level at which a CNR is the maximum based on identification information of a patient according to an embodiment.

In operation S1610, the CT image processing apparatus obtains the identification information of the patient who is a target of CT photographing. The CT image processing apparatus according to an embodiment may obtain the identification information of the patient through a user input, but is not limited thereto.

In operation S1620, the CT image processing apparatus generates a plurality of VMIs regarding the patient. The CT image processing apparatus according to an embodiment irradiates the patient with X-rays having different energy spectra, generates a CT image by detecting X-rays transmitted through a part of the patient that is a photographing target, and reconstructs the generated CT image, thereby generating the plurality of VMIs respectively corresponding to a plurality of energy levels. A method of generating the plurality of VMIs is the same as a method of operation S930 of FIG. 9, and thus a redundant description thereof is omitted.

In operation S1630, the CT image processing apparatus determines the VMI of the energy level at which the CNR is the maximum among the plurality of VMIs, based on previously stored information about the patient and the CNR. The CT image processing apparatus according to an embodiment may store information about the patient who has undergone CT photographing and provide information about the energy level at which the CNR is the maximum among the plurality of VMIs obtained through CT photographing. For example, the CT image processing apparatus may store a database of CNR information according to diagnosis of patients and photographing information in that the CNR the highest at an energy level of 67 keV for a patient A and the CNR is the highest at an energy level of 69 keV for a patient B.

The CT image processing apparatus may match the identification information of the patient obtained in operation S1610 and the information about the patients stored in the database and obtain information about the energy level at which the CNR is the maximum according to the matched patient information. For example, when the patient A performs CT photographing, the CT image processing apparatus may receive identification information of the patient A from the user and search for the database to see whether there is CNR information about the patient A. When there is a CT photographing record of the patient A and the CNR information in the database, the CT image processing apparatus may obtain information about an energy level at which the CNR of the patient A is the maximum from the database. The CT image processing apparatus may determine the VMI in which the CNR is the maximum among the plurality of VMIs generated in operation S1620 based on information about the energy level at which the CNR of the patient A obtained from the database is the maximum.

The CT image processing apparatus according to an embodiment may determine an image of an energy level at which the CNR is greater than a predetermined value as the VMI among the plurality of VMIs based on the previously stored information about the patient and the CNR.

In operation S1640, the CT image processing apparatus displays the VMI of the determined energy level.

According to the flowchart shown in FIG. 16, the CT image processing apparatus may determine the VMI of the energy level at which the CNR is the maximum among the plurality of VMIs, regardless of concentration and type of a contrast agent and size of an object. The embodiment shown in FIG. 16 may omit a separate processing procedure in case of a patient who has undergone CT photographing and follow-up photographing to see a progress of a lesion, thereby improving the user convenience.

The embodiments may be implemented as a software program including instructions stored in a computer-readable storage medium.

A computer may refer to a device configured to retrieve an instruction stored in the computer-readable storage medium and to operate, in response to the retrieved instruction, and may include an tomographic imaging apparatus according to embodiments.

The computer-readable storage medium may be provided in the form of a non-transitory storage medium. In this regard, the term 'non-transitory' means that the storage medium does not include a signal and is tangible, and the term does not distinguish between data that is semi-permanently stored and data that is temporarily stored in the storage medium.

In addition, the tomographic imaging apparatus or the method of controlling the tomographic imaging apparatus according to embodiments may be provided in the form of a computer program product. The computer program product may be traded, as a product, between a seller and a buyer.

The computer program product may include a software program and a computer-readable storage medium having stored therein the software program. For example, the computer program product may include a product (e.g. a downloadable application) in the form of a software program electronically distributed by a manufacturer of the tomographic imaging apparatus or through an electronic market (e.g., Google™, Play Store™, and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a terminal (e.g., the tomographic imaging apparatus), the computer program product may include a storage medium of the server or a storage medium of the terminal. Alternatively, in a case where a third device (e.g., a smartphone) that communicates with the server or the terminal is present, the computer program product may include a storage medium of the third device. Alternatively, the computer program product may include a software program that is transmitted from the server to the terminal or the third device or that is transmitted from the third device to the terminal.

In this case, one of the server, the terminal, and the third device may execute the computer program product, thereby performing the method according to embodiments. Alternatively, at least two of the server, the terminal, and the third device may execute the computer program product, thereby performing the method according to embodiments in a distributed manner.

For example, the server (e.g., a cloud server, an artificial intelligence (AI) server, or the like) may execute the computer program product stored in the server, and may control the terminal to perform the method according to embodiments, the terminal communicating with the server.

As another example, the third device may execute the computer program product, and may control the terminal to perform the method according to embodiments, the terminal communicating with the third device.

In a case where the third device executes the computer program product, the third device may download the computer program product from the server, and may execute the downloaded computer program product. Alternatively, the third device may execute the computer program product that is pre-loaded therein, and may perform the method according to the embodiments.

The above-described embodiments of the present disclosure may be embodied in form of a computer-readable recording medium for storing computer executable command languages and data. The command languages may be stored in form of program codes and, when executed by a processor, may perform a certain operation by generating a certain program module. Also, when executed by a processor, the command languages may perform certain operations of the disclosed embodiments.

While embodiments of the present disclosure have been particularly shown and described with reference to the accompanying drawings, it will be understood by those of ordinary skill in the art that various changes in form and details may be made therein without departing from the spirit and scope of the invention as defined by the appended claims. The disclosed embodiments should be considered in descriptive sense only and not for purposes of limitation.

What is claimed is:

1. A computed tomography (CT) image processing apparatus for processing a CT image of an object, the CT image processing apparatus comprising:
   a detector configured to detect X-rays having different energy spectra transmitted through the object and obtain raw data in each of energy ranges of the X-rays, through the detected X-rays;
   a processor configured to:
      generate a CT image by using the raw data obtained in each of the energy ranges of the X-rays,
      set a region of interest (ROI) on the CT image based on a user input,
      generate a plurality of virtual monochromatic images (VMIs) respectively corresponding to a plurality of energy levels by reconstructing the CT image according to calculation of a weighted average which is applied based on the raw data obtained in each of the energy ranges of the X-rays,
      measure a contrast-to-noise ratio (CNR) of the ROI, and
      determine a VMI at an energy level at which the measured CNR is at a maximum among the plurality of energy levels of the plurality of VMIs; and
   a display configured to display the determined VMI.

2. The CT image processing apparatus of claim 1, further comprising a user input unit configured to receive information about a type of a contrast agent from a user,
   wherein the processor is configured to measure a concentration of the contrast agent injected into the object in the ROI and determine the energy level at which the CNR is maximum based on the type of the contrast agent input through the user input unit and a relationship between the concentration of the contrast agent and the CNR.

3. The CT image processing apparatus of claim 2, further comprising
   a memory storing, in a look-up table (LUT), information about the relationship between the energy level and the CNR according to the type and the concentration of the contrast agent,
   wherein the processor is further configured to determine the VMI of the energy level at which the CNR is at a maximum according to the concentration of the contrast agent determined in the ROI and the type of the contrast agent, with reference to the LUT stored in the memory.

4. The CT image processing apparatus of claim 1, wherein the processor is further configured to measure a size of the object in the CT image and, based on the measured size of the object, determine the VMI of the energy level at which the CNR is at a maximum.

5. The CT image processing apparatus of claim 4, further comprising a memory storing, in a look-up table (LUT), information about a relationship between the energy level and the CNR, according to the size of the object,
   wherein the processor is further configured to determine a VMI of the energy level at which the CNR is at a maximum according to the measured size of the object, with reference to the LUT stored in the memory.

6. The CT image processing apparatus of claim 4, wherein the processor is further configured to measure the size of the object through sizes of various phantoms having diameters of different sizes.

7. The CT image processing apparatus of claim 1, further comprising a memory storing information about the energy level at which the CNR is at a maximum, according to information of a patient,
   wherein the processor is further configured to obtain identification information of the patient who is a target of CT photographing and, based on the information about the energy level stored in the memory, determine the VMI of the energy level at which the CNR is at a maximum according to the identification information of the patient.

8. A method of operating a computed tomography (CT) image processing apparatus, the method comprising:
   detecting X-rays having different energy spectra transmitted through the object and obtaining raw data in each of energy ranges through the detected X-rays;
   setting a region of interest (ROI) on the CT image based on a user input;
   generating a plurality of virtual monochromatic images (VMIs) respectively corresponding to a plurality of energy levels by reconstructing the CT image according to calculation of a weighted average which is applied based on the raw data obtained in each of the energy ranges of the X-ray;
   determining a contrast-to-noise ratio (CNR) of the ROI on the plurality of VMIs and determining a VMI at an energy level at which the determined CNR is at a maximum among the plurality of energy levels of the plurality of VMIs; and
   displaying the determined VMI.

9. The method of claim 8, wherein the determining of the VMI comprises:
   measuring a concentration of a contrast agent injected into the object in the ROI;
   receiving information about a type of the contrast agent from a user; and
   determining the energy level at which the CNR is at a maximum based on the type of the contrast agent and a relationship between the concentration of the contrast agent and the CNR.

10. The method of claim 9, wherein the CT image processing apparatus stores, in a look-up table (LUT), information about the relationship between the energy level and the CNR according to the type and the concentration of the contrast agent,
   wherein the determining of the VMI comprises determining a VMI at the energy level at which the CNR is at a maximum according to the concentration of the contrast agent determined in the ROI and the type of the contrast agent, with reference to the LUT stored in the CT image processing apparatus.

11. The method of claim 8, further comprising measuring a size of the object in the CT image,
    wherein the determining of the VMI comprises determining the VMI at the energy level at which the CNR is at a maximum based on the measured size of the object.

12. The method of claim 11, wherein the CT image processing apparatus stores, in a look-up table (LUT), information about a relationship between the energy level and the CNR according to the size of the object,
    wherein the determining of the VMI comprises determining the VMI of the energy level at which the CNR is at a maximum according to the measured size of the object, with reference to the previously stored LUT.

13. The method of claim 11, wherein the measuring of the size of the object comprises measuring the size of the object through sizes of various phantoms having diameters of different sizes.

14. The method of claim 8, the CT image processing apparatus stores information about the energy level at which the CNR is at a maximum according to information of a patient,
    wherein the determining of the VMI comprises:
        obtaining identification information of the patient who is a target of CT photographing; and
        based on the information about the energy level stored in the memory, determining the VMI at the energy level at which the CNR is at a maximum according to the identification information of the patient.

15. A computer program product comprising a non-transitory computer readable storage medium, wherein the non-transitory computer readable storage medium comprises instructions to perform:
    detecting X-rays having different energy spectra transmitted through the object and obtaining raw data in each of energy ranges through the detected X-rays;
    setting a region of interest (ROI) on the CT image based on a user input;
    generating a plurality of virtual monochromatic images (VMIs) respectively corresponding to a plurality of energy levels by reconstructing the CT image according to calculation of a weighted average which is applied based on the raw data obtained in each of the energy ranges of the X-ray;
    determining a contrast-to-noise ratio (CNR) of the ROI on the plurality of VMIs and determining a VMI at an energy level at which the determined CNR is at a maximum among the plurality of energy levels of the plurality of VMIs; and
    displaying the determined VMI.

\* \* \* \* \*